United States Patent
McLaren et al.

(10) Patent No.: US 10,632,142 B2
(45) Date of Patent: Apr. 28, 2020

(54) TREATMENT OF COLITIS WITH RESISTANT STARCH

(71) Applicant: McPharma Biotech Inc., Carberry (CA)

(72) Inventors: Derek McLaren, Carberry (CA); Earl McLaren, Carberry (CA)

(73) Assignee: McPharma Biotech Inc., Carberry, Manitoba (CA)

( * ) Notice: Subject to any disclaimer, the term of this patent is extended or adjusted under 35 U.S.C. 154(b) by 0 days.

(21) Appl. No.: 16/271,089

(22) Filed: Feb. 8, 2019

(65) Prior Publication Data
US 2019/0262382 A1    Aug. 29, 2019

Related U.S. Application Data

(60) Provisional application No. 62/625,548, filed on Feb. 2, 2018.

(51) Int. Cl.
| | | |
|---|---|---|
| *A61K 31/718* | (2006.01) | |
| *A61P 1/14* | (2006.01) | |
| *A61P 1/12* | (2006.01) | |
| *A61P 1/06* | (2006.01) | |
| *A61P 1/04* | (2006.01) | |

(52) U.S. Cl.
CPC ............ *A61K 31/718* (2013.01); *A61P 1/04* (2018.01); *A61P 1/06* (2018.01); *A61P 1/12* (2018.01); *A61P 1/14* (2018.01)

(58) Field of Classification Search
None
See application file for complete search history.

(56) References Cited

U.S. PATENT DOCUMENTS

2007/0059431 A1* 3/2007 Simon ............... C08B 30/12
  426/658
2015/0250814 A1* 9/2015 McLaren ............ A61K 31/718
  514/60

OTHER PUBLICATIONS

Bassaganya-Rierra, J. Nutr. 141: 1318-1325, 2011. (Year: 2011).*

* cited by examiner

*Primary Examiner* — Layla D Berry
(74) *Attorney, Agent, or Firm* — Michael R. Williams; Ryan W. Dupuis; Ade + Company Inc.

(57) ABSTRACT

Resistant potato starch is demonstrated to have therapeutic effects on ulcerative colitis through attenuation of diarrhea, repair or reduction of intestinal damage, modulation of local gene expression and treatment of intestinal dysbiosis. Administering resistant potato starch in pigs pre-exposed to colitis improved fecal score although use of resistant potato starch as a preventive measure did not prevent diarrhea associated with induction of colitis and in fact impaired the ability of the resistant potato starch to treat ulcerative colitis.

6 Claims, 9 Drawing Sheets

Specification includes a Sequence Listing.

TREATMENT OF COLITIS WITH RESISTANT STARCH

PRIOR APPLICATION INFORMATION

The instant application claims the benefit of U.S. Provisional Patent Application 62/625,548, filed Feb. 2, 2018.

BACKGROUND OF THE INVENTION

Inflammatory Bowel Disease (IBD) is an umbrella term used to describe disorders that involve chronic inflammation of the digestive tract. IBD is generally attributed to an inappropriate immunologic response to otherwise commensal flora in a genetically susceptible host. Symptoms of IBD most commonly include fever, vomiting, diarrhea, bloody stool, abdominal pain and weight loss. Types of IBD include ulcerative colitis and Crohn's disease.

Ulcerative colitis causes long-lasting inflammation and sores (ulcers) in the innermost lining of the large intestine (colon) and rectum. UC is usually characterized by inflammation of the colon and the rectum.

Crohn's disease is characterized by inflammation of the lining of the digestive tract, which often spreads deep into affected tissues. CD commonly manifests as inflammation of the small intestine, but can affect other parts of the body as well.

UC and CD are commonly regarded as autoimmune diseases, with evidence suggesting they are the result of misdirected immune response. The etiology of IBD appears to involve complex interactions of genetic predisposition, environmental factors, disruption of the intestinal microbiome and an overly aggressive immune response. In addition, evidence linking the ability of intestinal epithelial cells to modify the mucosal immune response, may suggest an invasive bacterial pathway. Imbalance in intestinal microbiota of gut friendly bacteria destroyed by antibiotics as well as opportunistic pathogens are implicating factors as well. Specifically, patients with IBD have been reported to have an abnormal gut microbiota. Whether this altered flora is the cause or the result of chronic inflammation remains unclear.

In this context, animal models have been established to provide a uniquely accurate and tractable model for studying the gut microbiota, including the molecular and cellular mechanisms driving chronic intestinal inflammation (Panwala et al., 1998; Shah et al., 1998; Pizarro et al., 2003; Sartor, 2006; Wirtz et al., 2007). The models of inflammatory bowel disease facilitate a mechanistic evaluation of the contribution of the gut microbiota to the initiation and perpetuation of chronic intestinal inflammation, as occurs in human IBD (Sartor, 2006).

There are numerous emerging therapeutic strategies, which may be useful in the alleviation of chronic intestinal inflammation, including dietary supply of non-digestible saccharides such as resistant starch (RS), inulins, fructo-oligosaccharides among others, which are carbohydrate food ingredients designated as prebiotics (Cummings and Englyst, 1987; Cummings et al., 1997; Higgins and Brown, 2013). RS, also known as Digestion Resistant Starch, is defined as the sum of starch and starch digestion products that are not digested in the small intestine but instead reach the large intestine as a fermentable fiber substrate. Resistant starch represents a diverse range of indigestible starch-based dietary carbohydrates that are not digested and absorbed in the upper digestive tract and, so, pass into the large bowel, where they undergo microbial fermentation (Asp, 1987; Topping and Clifton, 2001; Higgins and Brown, 2013).

Resistant starch has been investigated in the past for its effects on bowel health (pH, epithelial thickness, and apoptosis of colorectal cancer cells), reduction in postprandial glycemia; increased insulin sensitivity; and effects on the gut microbiome (Higgins and Brown, 2013).

It is important to note however that all resistant starch is not equal. Specifically, there is exceptional diversity encountered among RS varieties. Specifically, RS varieties originating from different plant sources and/or manufactured with alternative processing technologies will possess unique physiochemical properties.

For example, a comparison of the structural properties of high amylose corn starch and potato starch (Leszczynski, 2004. Pol. J. Food Nutr. Sci 13/54: 37-50) teaches that the starch granule surface features are determined by the botanical origin of starch and, along with an increasing size of granules, they affect the specific surface area of starch. The specific surface area is diversified depending on the type of starch and ranges from e.g. 0.243 $m^2/g$ in the case of potato starch granules with type B crystallinity to 0.687 $m^2/g$ in the case of type A maize starch granules . . . . The specific surface area of starch granules and pore volume are correlated with gelatinization temperature and the viscosity of pastes obtained. The specific surface area of starch granules, as well as the number and size of pores, are also linked with the ability of starch to adsorb different substances, including protein compounds and enzymes.

The microbial complex in the colon, comprising apparently $10^{14}$ microbes of several hundred species, represents a large ecosystem, which in the right composition has a beneficial effect on the host. In this regard, the intestinal microbiota, with their immunological potency, may play an essential role in intestinal barrier resistance to ulcerative colitis (UC) (Butzner et al., 1996), and could be important in promoting large bowel health and preventing IBD among other gut ailments (Topping and Clifton, 2001). Studies utilizing mouse models of colitis have demonstrated a potential role of RS in IBD by partially preventing or ameliorating clinical disease or disease severity and prevention of inflammatory lesions (Bassaganya-Riera et al., 2011; Le Leu et al., 2013). This study therefore seeks to investigate resistant starch (MSPrebiotic®) as a potential preventive and or therapeutic tool for ulcerative colitis in a pig model of experimental colitis.

SUMMARY OF THE INVENTION

According to a first aspect of the invention, there is provided a method of treating Inflammatory Bowel disease in an individual in need of such treatment comprising administering to said individual an effective amount of resistant potato starch.

In some embodiments of the invention, the individual in need of such treatment is an individual who has been diagnosed with or who is suspected of having ulcerative colitis.

In some embodiments of the invention, the effective amount of the resistant potato starch is administered to the individual on a schedule or regimen.

In some embodiments of the invention, the schedule or regimen is daily administration for a period of time.

In some embodiments of the invention, the period of time is daily for about two weeks, daily for about three weeks, daily for about four weeks or daily for about five weeks.

In some embodiments of the invention, the effective amount of the resistant potato starch is administered until the severity of one or more symptoms associated with ulcerative colitis, specifically, a flare of ulcerative colitis, has reduced or improved. For example, such an improvement or reduction of severity of a symptom associated with ulcerative colitis may be decreased or reduced abdominal pain; fewer instances of abdominal pain; longer periods of time between instances of abdominal pain; reduced or less frequent abdominal sounds; reduced or less frequent bloody stools; longer periods of time between instances of bloody stools; less frequent or less severe diarrhea; longer periods of time between incidents of diarrhea; reduced fever; reduced or lessened rectal pain; or longer period of time between incidents of rectal pain.

In some embodiments of the invention, the effective amount is administered until episodes of diarrhea have stopped and then treatment is discontinued. Specifically, as discussed herein, prophylactic treatment or prevention of ulcerative colitis is ineffective when administering an amount of resistant potato starch that is effective as an intervention or treatment. In fact, administration of resistant potato starch prior to a flare of ulcerative colitis may impair or reduce or even eliminate the therapeutic effects of resistant potato starch.

Accordingly, in one aspect of the invention, there is provided a method of treating a flare of ulcerative colitis in an individual who has been diagnosed with ulcerative colitis comprising administering to the individual an effective amount of resistant potato starch until at least one symptom associated with the flare of colitis has improved or ceased and then stopping treatment.

In another embodiment of the invention, there is provided a method of treating a flare of ulcerative colitis in an individual who has been diagnosed with ulcerative colitis comprising administering to the individual an effective amount of resistant potato starch until incidents of diarrhea have ceased and then stopping treatment.

In another embodiment of the invention, there is provided a method of treating a flare of ulcerative colitis in an individual who has been diagnosed with ulcerative colitis comprising administering to the individual an effective amount of resistant potato starch until incidents of diarrhea have ceased and then stopping treatment, with the proviso that the individual has not been administered a regimen of resistant potato starch immediately prior to the flare of ulcerative colitis.

In some embodiments of the invention, the resistant potato starch is administered daily for a period of 2-5 weeks.

As discussed herein, the effective amount may be for example 2 to 40 g or 2 to 30 g or 2 to 20 g or 5 to 40 g or 5 to 30 g or 5 g to 20 g or 10 to 20 g of resistant potato starch, as discussed herein.

DESCRIPTION OF THE PREFERRED EMBODIMENTS

Figure 1:
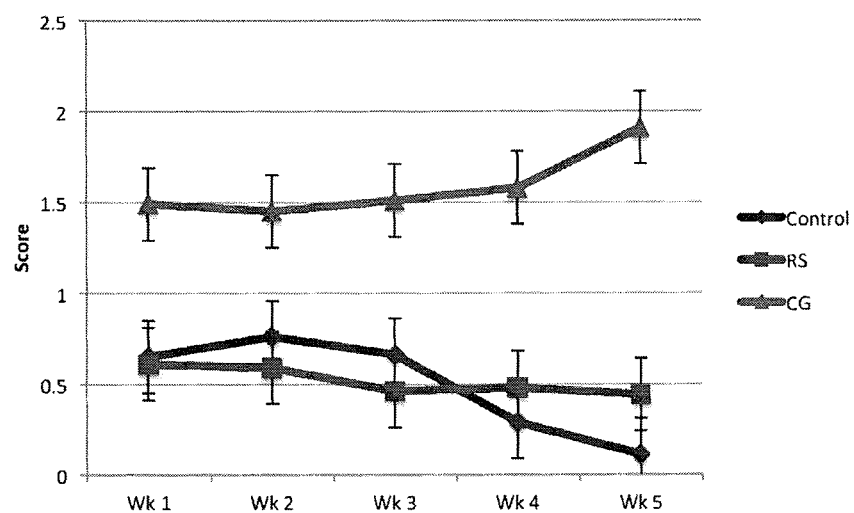
FIG. 1. Effect of degraded carrageenan gum (CG) and resistant starch (RS; MSPrebiotic) on fecal score as determined by stool consistency. CG was administered from d 1 of the experiment. Control=pigs received basal diet only, CG=pigs received 1% CG only in drinking water on daily basis, RS=pigs received basal diet and one scoop (10 g) of MSPrebiotic during the first 14 days of the experiment after which the amount of MSPrebiotic was adjusted to one scoop and half (15 g) until the end of the experimental period. All pigs were euthanized on day 40. Severity of diarrhea was characterized using an established fecal consistency (FC) score system in pigs (0, normal; 1, soft feces; 2, mild diarrhea; 3, severe diarrhea.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

We investigated protective and therapeutic effects of RS (MSPrebiotic®) in a pig model of experimental colitis.

MSP Starch Products Inc, manufactures MSPrebiotic® Resistant Potato Starch, an unmodified RS type 2 starch that is a *Solanum Tuberosum* Extract preparation of food grade quality for animal and human food application. While MSPrebiotic®, which contains 7 g of fiber in 10 g of product is used in the trials and experiments discussed herein, it is important to note that as discussed herein, another suitable resistant potato starch or potato resistant starch, that is, another unmodified RS type 2 potato starch, comprising at least 60% resistant starch or at least 65% resistant starch or at least 70% resistant starch or at least 75% resistant starch or at least 80% resistant starch of total extract or total potato extract may be used. That is, the extract itself may comprise 80% resistant starch on a weight to weight basis.

As discussed herein, we demonstrate that inclusion of RS as a therapy improved fecal consistency, modulated local inflammation, and improved histological structure of the large intestines. Also, inclusion of RS either as a prevention or therapeutic measure influenced bacterial structure, especially in the large intestines. Linear discriminant analysis (LDA) effect size (LEfSe) revealed significant differences in bacterial groups between colitic (CG) and non-colitic pigs as well as both in protective and therapeutic groups in various intestinal segments. *Desulfovibrio, Mucispirillum, Fusobacterum*, Enterobacteriaceae, Deferribacteraceae, Fusobacteria and Deferribacteres were significantly enriched in CG group. In contrast, *Bifidobacterium, Peptococcus, Succinivibrio, Ruminococcus, Campylobacter, Xanthomonadales*, Mollicutes, Aeromonadales and other taxa were significantly enriched in the intestinal mucosa of control or as a therapeutic measure, but no such significant taxa were observed in the protective group. The observed changes in bacterial composition were accompanied by significant differences in various functional gene contents as predicted using PICRUSt.

In Experiment 1, the microbiota profile and local immune responses in pigs exposed to CG-induced colitis and in pigs supplemented with RS with no colitis was investigated, as discussed herein. The treatments were: 1; control (basal diet only), 2; CG (as in 1 and 1% CG starting from wk 1 of the study), and 3; RS (as in 1 and MSPrebiotic (RS) starting from wk 1 of the study). Pigs in treatment one received basal diet only throughout the experimental period, pigs in treatment two received basal diet and 1% CG solution throughout the experimental period; and pigs in treatment three received basal diet and one scoop (10 g) of MSPrebiotic during the first 14 days of the experiment after which the amount of MSPrebiotic was adjusted to one scoop and half (15 g) until the end of the experimental period.

In Experiment 2, the role of resistant starch (MSPrebiotic) as a potential preventive or therapeutic tool for ulcerative colitis in a pig model of experimental colitis was investigated. The treatments were: 1; CG (as used in experiment one), 2; RST (as in CG and MSPrebiotic starting from wk 3 of the study), and 3; RSP (as in RS and 1% CG starting from wk 3 of the study). In the RST group, pigs received CG alone during the first 14 d of the experiment and MSPrebiotic (RS) was introduced (15 g) from 15th day of the study up to the end of the experimental period. In this case MSprebiotic (RS) was used as a therapy for CG-induced colitis and the purpose was to investigate whether RS could induce remission or reduce the severity of colitis in pigs with active colitis. In the RSP group, pigs received 10 g daily RS alone for the first 14 d of the study, and CG was introduced at the start of d 15 until the end of the experimental period. Also starting from d 15 of the experiment, the amount of RS was adjusted to 15 g/d to compensate for the changes in growth of the pigs. Here the RS was used for prevention or protection against CG-induced colitis and the aim was to investigate whether consumption of RS can protect healthy individuals from developing colitis.

Our results demonstrate therapeutic effects of RS in CG-induced colitis through attenuation of diarrhea, intestinal damage, modulation of local gene expression and intestinal dysbiosis. Administering RS in pigs with CG-induced colitis improved fecal score; however, while the use of RS as a preventative measure initially attenuated diarrhea (in comparison to CG pigs), this improvement with preventative RS is lost over time, as shown in FIG. 4.

Figure 4:
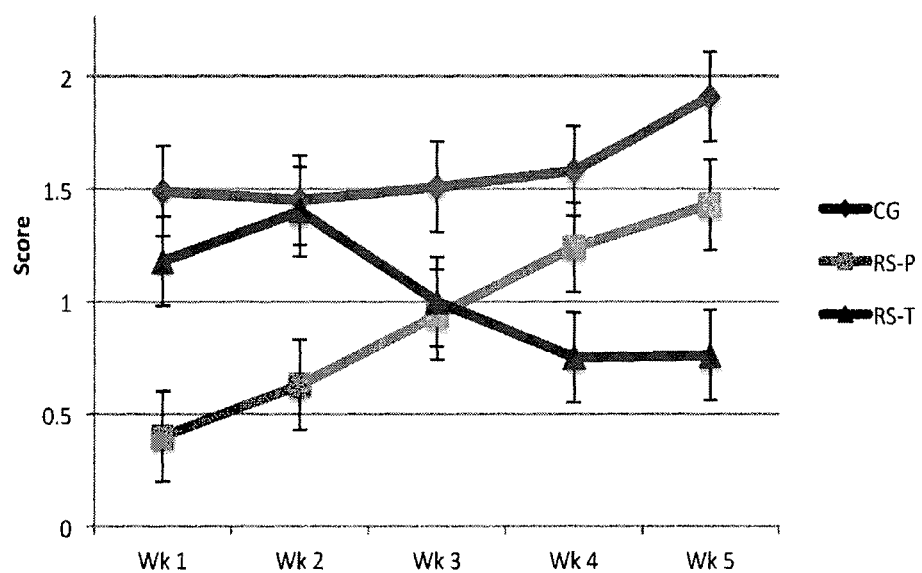
FIG. 4. Therapeutic or/and protective effect of resistant starch (RS; MSPrebiotic) on fecal score as determined by stool consistency in pigs exposed to degraded carrageenan gum (CG)-induced colitis. CG was administered from d 1 of the experiment. Control=pigs received basal diet only, CG=pigs received 1% CG only in drinking water on daily basis, RSP=pigs received 10 g daily RS alone for the first 14 d of the study and CG was introduced at the start of d 15 until the end of the experimental period. Also starting from d 15 of the experiment, the amount of RS was adjusted to 15 g/d, RST=pigs received CG alone during the first 14 d of the experiment and RS was introduced (15 g) from 15th day of the study up to the end of the experimental period. Severity of diarrhea was characterized using an established fecal consistency (FC) score system in pigs (0, normal; 1, soft feces; 2, mild diarrhea; 3, severe diarrhea.

Specifically, as can be seen in FIG. 4, at weeks 1 and 2, both the CG group and the RS-T group are being administered CG but no RS; the RS-P group is receiving 10 g/day RS but no CG. Consequently, during those two weeks, both CG and RS-T have fecal scores corresponding to soft feces-mild diarrhea, as was seen for the CG group in Experiment 1 (FIG. 1). Similarly, the fecal scores for the RS-P group is similar to that seen with the control and the RS group in FIG. 1.

At the end of two weeks, the CG group continues to receive CG only for the duration of the experiment. However, the RS-P group is administered CG while the dose of RS is increased to 15 g/day to compensate for animal growth. Similarly, the RS-T group continues to receive CG but is now administered RS at 15 g/day for the duration of the experiment.

Figure 3:
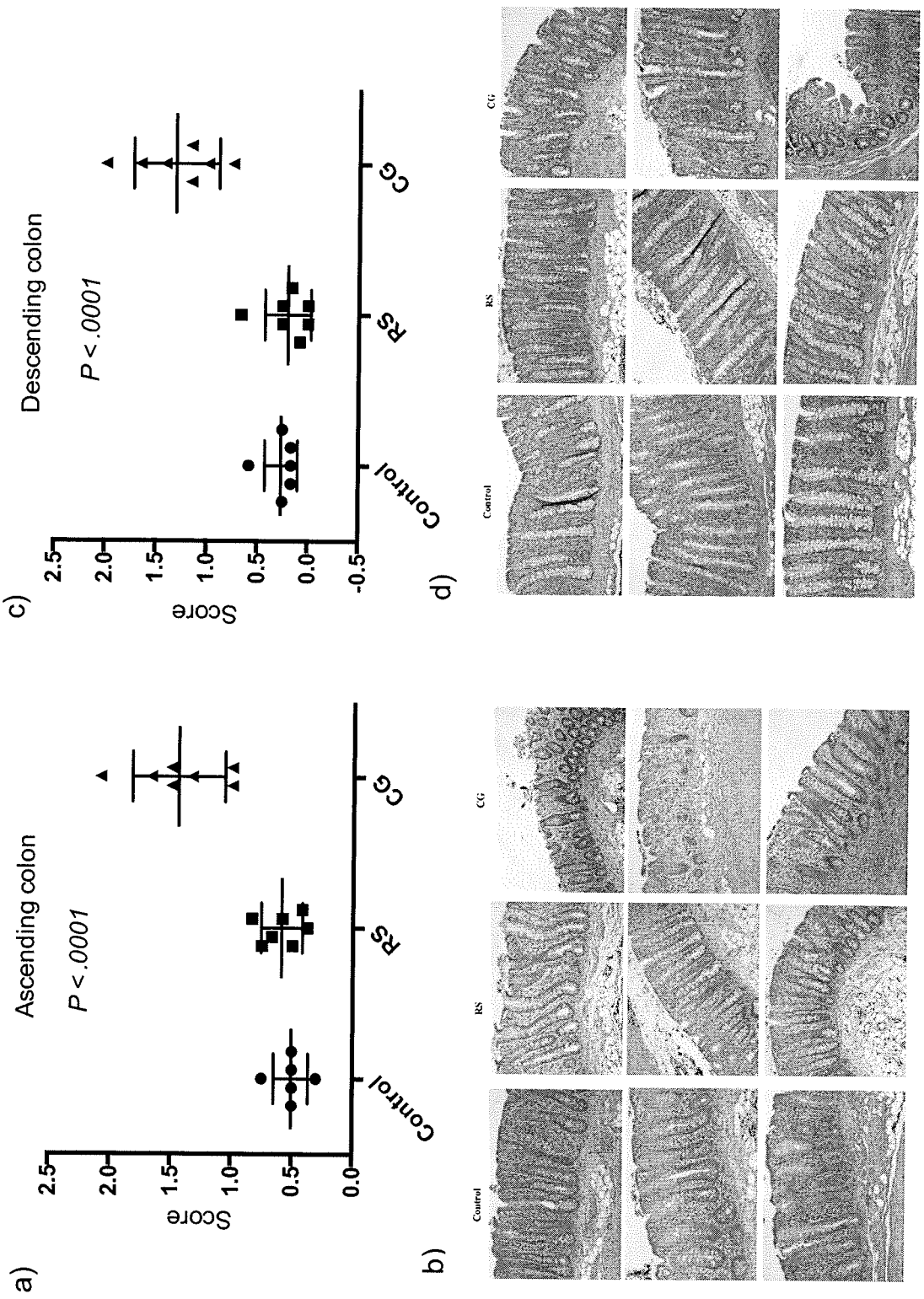
FIG. 3. Effect of degraded carrageenan gum (CG) and resistant starch (RS; MSPrebiotic) on histological structure. a) and b) shows histological score and the extent of histological damage, respectively in the ascending colon. c) and d) shows the histological score and the extent of histological damage, respectively in the descending colon. CG was administered from d 1 of the experiment. Control=pigs received basal diet only, CG=pigs received 1% CG only in drinking water on daily basis, RS=pigs received basal diet and one scoop (10 g) of MSPrebiotic during the first 14 days of the experiment after which the amount of MSPrebiotic was adjusted to one scoop and half (15 g) until the end of the experimental period. All pigs were euthanized on day 40.

As expected and consistent with FIG. 1, the fecal scores of the CG group continue to worsen over time, as can be seen in FIG. 3.

However, the results observed for the RS-P and RS-T groups are surprisingly different. Specifically, as can be seen from FIG. 3, the administration of RS as a therapeutic intervention results in improved fecal scores, which stabilize after two weeks.

Given the treatment of experimental colitis based on improved fecal scores seen in the RS-T group even with continuing administration of CG, one would expect that the RS-P group would show some initial protection against experimental colitis, possibly preventing experimental colitis from developing at all or displaying only a mild reaction to the CG on initial administration, followed by an improvement in fecal scores which would then stabilize, as was seen in the RS-T group.

However, at week 3, the fecal scores of the RS-T and RS—P groups are approximately the same. As will be appreciated by one of skill in the art, this is not consistent with a minor reaction to CG as a result of protection from the prior administration of RS.

This is borne out in the results for week 4, as the fecal scores of the RS-T group continue to improve and in fact appear to stabilize while the fecal scores in the RS-P group continue to worsen in week 4 and again in week 5.

As such, contrary to expectations, the RS-P group shows no true protection against the development of colitis, although it does appear to delay or slow the development of more severe symptoms. However, the RS-P group, where there is continuing administration of RS, does not show any reduction in the severity of symptoms over time, contrary to what is seen in the RS-T group.

As such, it is clear that RS cannot prophylactically treat or prevent a colitis flare. In fact, administration of RS on a schedule or regimen prior to a flare of colitis, which is tested in the RS-P group, appears to actually prevent the therapeutic effects of RS-T seen in that group.

It is noted that this difference in fecal scores based on whether the RS is administered prior to or post induction of experiment colitis is supported by the fact that, as discussed herein, the inflammatory responses, mucin gene expression and differences in bacterial taxa are significantly different.

As discussed herein, cytokines play an important role in disease progression, and increased levels of pro-inflammatory cytokines such as IL-8, IFN-γ, IL-1β, IL-12p40 and others, are most commonly involved in innate immune pathogenesis of IBD, and have been reported in patients with IBD, and in mice and pigs with DSS-induced colitis (Daig et al., 1996; Egger et al., 2000; Lee et al., 2009). However, as discussed below, RS significantly reduced local expression of IFN-γ, a known driver of inflammatory responses, and IL-8, a chemokine that contributes to inflammatory-mediated pathology through recruitment of neutrophils (Nielsen et al., 1997), and also increased the expression of TGF-β and Foxp3, which play major roles in maintaining immune homeostasis. With regard to inflammatory responses, IL-17 has a controversial role as an effector or protector (Fuss, 2011). Some studies have shown IL-7's pathogenic role (Fujino et al., 2003), while conversely it has been reported to have a protective role in different models of IBD (Yang et al., 2008; O'Connor et al., 2009; Eken et al., 2014). Whereas inclusion of RS down regulated IL-17 in some intestinal segments compared to CG, there was an up regulation in the cecum of RSP and RST pigs, which could be explained by the perceived dual role of IL-17. The differences in expression of selected inflammatory-related compounds in different sections of the digestive tract in the different groups can be seen in FIG. 5.

Regarding mucin gene expression, the mucus layer acts as a physical barrier to protect and maintain mucosal epithelial integrity (Tai et al., 2007). Mice lacking the capacity to produce mucin are known to spontaneously develop a colitis-like phenotype, and are also more susceptible to chemically induced colitis (Van der Sluis et al., 2006; Johansson et al., 2008). In addition, decreased expression of mucin genes has been reported during DSS-induced colitis in both mice and porcine models (Tai et al., 2007; Lee et al., 2009b). In the current study, relative gene expression of MUC1 and MUC2 were found to be decreased as a result of CG-induced colitis in the ileum and cecum; however, this was inhibited and restored by protective and therapeutic use of RS in the ileum. However, only MUC1 was positively influenced by protective and therapeutic use of RS in the ileum and cecum, whereas the protective and therapeutic use of RS had negative effects on the expression of MUC2 in the ascending colon. However, only RS-T had positive effects on expression of MUC2 in the descending colon, while RS-P in fact had a negative effect on MUC2 expression in the descending colon compared to the GC group In this case, the positive effects of RS were more pronounced in the membrane-bound mucin MUC1 which plays a role in cell signaling (Bergstrom and Xia, 2013) and Injury repair (Hoebler et al., 2006; Jiang et al., 2011), compared to the secreted form, MUC2. Generally, an increase in the expression of mucus genes can be considered a beneficial response, contributing to an enhanced mucus barrier (Boltin et al., 2013; Dorofeyev et al., 2013; Pastorelli et al., 2013). Also, although different protective or therapeutic measures may fail to directly stimulate the rejuvenation of mucosal barrier system, they may indirectly help in promoting remission in IBD conditions through manipulation of the luminal environment (McGuckin et al., 2009). We found that feeding pigs the RS-containing diet was linked to a beneficial manipulation of the gut microbiota, reflected by substantial shifts in the composition of mucosa-associated microbiota. As discussed below, principal coordinate analysis (PCoA) plots revealed significant differences between CG, the control, and RS groups, especially in the large intestines. The results suggest differences in the overall microbiota structure between healthy pigs and pigs with CG-induced colitis. Of interest was the fact that RSP and RST bacterial composition differed from that of CG in the large intestines, as discussed in greater detail below and as shown in FIGS. 7-10. The changes in bacterial structure were confirmed by linear discriminant analysis (LDA) effect size (LEfSe), where we observed significant enrichment of various bacterial taxa in specific groups. The association of some members of Proteobacteria, especially members of Gammaproteobacteria, with CG-induced colitis agrees with our recent findings (Munyaka et al., 2016b), as well as previous reports by others in IBD patients and in animals with IBD or experimental IBD (Sellon et al., 1998; Darfeuille-Michaud et al., 2004; Schuppler et al., 2004; Mylonaki et al., 2005; Kotlowski et al., 2007; Lupp et al., 2007; Xenoulis et al., 2008; Sepehri et al., 2011; Wright et al., 2015). In addition, members of Deferribacteres and Fusobacteria including *Mucispirillum* and *Fusobacterium* were also consistently associated with CG-induced colitis, especially in the large intestines. Interestingly, Deferribacteres and Fusobacteria were completely absent in the control, RS, and in the RS-T and RS—P groups, suggesting their strong association with colitic conditions, and merit of use of MSPrebiotic. Other studies in pigs also support beneficial effects of RS feeding with an increase in the growth of microbial populations producing SCFA and inhibition of a range of potentially pathogenic microbial species (Haenen et al., 2013). Also, Succinivibrionaceae was enriched in all intestinal segments only in the RS based treatments, suggesting its strong association with the beneficial effects of RS.

Generally, inclusion of RS increased the abundance of bacteria associated with RS fermentation including members of Bifidobacteriaceae, *Ruminococcus* and *Bifidobacterium*. However, we also observed large increases in bacteria not directly involved in RS fermentation, which may help in modulating the gastrointestinal environment through attenuation of inflammation or mucosa regeneration. Nevertheless, it is worth noting that, compared to CG and RS-T, there were no significant taxa associated with the RS-P group across the intestinal segments supporting the conclusion of lower efficacy of RS as a protective measure in modulating gut microbiota at lower taxonomical levels in our model of colitis. This was also supported by observations made at microbiota functional level, as very few microbial functional pathways or activities were enriched in the RS-P group compared to other groups, again indicating lower effects observed during the use of RS as a protective measure.

As discussed herein and as summarized above, use of RS as a treatment significantly inhibited histological damage, attenuated expression of pro inflammatory cytokines, and also modulated intestinal bacterial dysbiosis and gene functional content following CG challenge. However, the protective effects were less effective compared to the therapeutic effects. As discussed above, this surprising discovery is supported by the observed differences between the two treatment groups.

While not wishing to be bound to a particular theory or hypothesis, therapeutic restoration of mucosal barrier function could improve pathophysiology and clinical outcomes in IBD. One of the main histological pathophysiology of models of colitis is profound colonic inflammation characterized by crypt shortening and destruction, mucosal ulceration, erosions, and infiltration of immune cells into the mucosal tissue, which is accompanied by an increase in pro-inflammatory cytokines (Kwon et al., 2005; Ghia et al., 2007a; Ghia et al., 2007b; Ghia et al., 2009; Lee et al., 2009b; Laroui et al., 2012; Rabbi et al., 2014; Munyaka et al., 2015; Munyaka et al., 2016a). However, whereas pigs exposed to CG-induced colitis showed crypt shortening and destruction, mucosal ulcerations and up regulation of pro inflammatory cytokines such as, IL-1β, IL-8, IFN-γ, the therapeutic effects of RS were evident in diminishing the damage, and in modulating inflammatory responses, supporting the use of RS in attenuating and reversing CG-induced harmful effects. Notably, an RS-containing diet was also recently shown to reduce inflammation, and restore the architecture of colonic lamina propria in a rat model of colitis-associated colorectal cancer (Hu et al., 2016).

In summary, inconsistent with what is predicted by the literature, we find that RS administration as a preventative measure and as a therapeutic measure produce different outcomes. Specifically, RS—P is unable to effectively treat diarrhea while RS-T improves all aspects of colitis. Consistent with the differences in symptoms, RS-T produces a different constellation of changes in bacterial population, inflammation markers, and gene expression, further highlighting the unique properties of delivering RS to interrupt colitis flare ups. It is unclear why pre-administration with RS is ineffective but could be due to transient changes in the microbiome, a hypothesis that is supported by our data.

According to an aspect of the invention, there is provided a method of treating Inflammatory Bowel disease in an individual in need of such treatment comprising administering to said individual an effective amount of resistant potato starch.

In some embodiments of the invention, the individual in need of such treatment is an individual who has been diagnosed with or who is suspected of having ulcerative colitis, for example, an individual who is currently suffering from a flare or attack of ulcerative colitis.

Ulcerative colitis typically varies between periods when the disease is active, or flaring up, and when it is in remission (few or no symptoms). A flare of ulcerative colitis may cause frequent or urgent bowel movements, diarrhea, bloody stool and/or abdominal pain, as well as fatigue, lack of appetite and weight loss.

The duration, severity and frequency of flares of colitis depend on several factors. For example, changes in diet can lead to a flare and while stress does not appear to cause flares of colitis, stress can lead to greater severity of symptoms. As such, some individuals may go several years between flares while others may have multiple flares within a one year period.

In some embodiments of the invention, the effective amount of the resistant potato starch is administered to the individual on a schedule or regimen.

In some embodiments of the invention, the schedule or regimen is daily administration for a period of time.

In some embodiments of the invention, the period of time is daily for about two weeks, daily for about three weeks, daily for about four weeks, daily for about five weeks, daily for about six weeks, daily for about seven weeks or daily for about eight weeks.

Alternatively, the period of time may be 2-8 weeks, 3-8 weeks, 4-8 weeks, 5-8 weeks, 6-8 weeks, 2-7 weeks, 3-7 weeks, 4-7 weeks, 5-7 weeks, 2-6 weeks, 3-6 weeks, 4-6 weeks, 2-5 weeks, 3-5 weeks or 2-4 weeks.

It is of note that "daily for about two weeks" does not necessarily mean that administration must be every day but may be for example 6 out of 7 days, 5 out of 7 days, 5 out of 6 days, 4 out of 5 days, 3 out of 4 days or the like. However, as will be apparent to those of skill in the art, better results will be obtained. Furthermore, for example, "two weeks" does not necessarily mean exactly 14 days but may mean 10 days, 11 days, 12 days, 13 days, 14 days, 15 days, 16 days, 17 days, 18 days, 19 days or the like.

In some embodiments of the invention, the effective amount of the resistant potato starch is administered until the severity of one or more symptoms associated with ulcerative colitis, specifically, a flare of ulcerative colitis, has reduced or improved. For example, such an improvement or reduction of severity of a symptom associated with ulcerative colitis may be decreased or reduced abdominal pain; fewer instances of abdominal pain; longer periods of time between instances of abdominal pain; reduced or less frequent abdominal sounds; reduced or less frequent bloody stools; longer periods of time between instances of bloody stools; less frequent or less severe diarrhea; longer periods of time between incidents of diarrhea; reduced fever; reduced or lessened rectal pain; or longer period of time between incidents of rectal pain.

In some embodiments of the invention, the improved symptom is decreased or reduced abdominal pain; fewer instances of abdominal pain; longer periods of time between instances of abdominal pain; reduced or less frequent abdominal sounds; reduced or less frequent bloody stools; longer periods of time between instances of bloody stools; less frequent or less severe diarrhea; or longer periods of time between incidents of diarrhea.

In some embodiments of the invention, the improved symptom is reduced or less frequent bloody stools; longer periods of time between instances of bloody stools; less frequent or less severe diarrhea; or longer periods of time between incidents of diarrhea.

In some embodiments of the invention, the effective amount is administered until episodes of diarrhea have stopped and then treatment is discontinued.

Specifically, as discussed herein, prophylactic treatment or prevention of ulcerative colitis with an effective amount of resistant potato starch is not effective. In fact, administration of resistant potato starch prior to a flare of ulcerative colitis may impair or reduce or even eliminate the therapeutic effects of resistant potato starch.

Accordingly, in one aspect of the invention, there is provided a method of treating a flare of ulcerative colitis in an individual who has been diagnosed with ulcerative colitis and who is experiencing a flare or attack of ulcerative colitis comprising administering to the individual an effective amount of resistant potato starch until at least one symptom associated with the flare of colitis has improved or ceased and then stopping treatment.

As discussed herein, preventative administration of resistant potato starch failed to treat the symptoms associated with a colitis flare in the animal model system. Specifically, as discussed herein, preventative administration appeared to slow disease progression but offered no stable relief from symptoms as was shown with therapeutic administration.

As such, as discussed herein, the data demonstrates that preventative treatment of ulcerative colitis with resistant potato starch is ineffective. Consequently, an individual who suffers from colitis who has treated a flare of colitis with resistant potato starch should stop treatment with the resistant potato starch as soon as symptoms have subsided and stabilized because presence of resistant potato starch prior to a colitis flare or attack impairs or eliminates the therapeutic effects of the resistant potato starch, as discussed herein.

As such, for treatment, it is important that the individual with colitis not be taking resistant potato starch prophylactically.

In another embodiment of the invention, there is provided a method of treating a flare of ulcerative colitis in an individual who has been diagnosed with ulcerative colitis or who is currently suffering from a flare or attack of ulcerative colitis comprising administering to the individual an effective amount of resistant potato starch until incidents of diarrhea have ceased and then stopping treatment.

In another embodiment of the invention, there is provided a method of treating a flare of ulcerative colitis in an individual who has been diagnosed with ulcerative colitis comprising administering to the individual an effective amount of resistant potato starch until incidents of diarrhea have ceased and then stopping treatment, with the proviso that the individual has not been administered a regimen of resistant potato starch immediately prior to the flare of ulcerative colitis.

In some embodiments of the invention, resistant potato starch has not been administered to the individual for at least two weeks prior to the colitis flare.

In some embodiments of the invention, the resistant potato starch is administered daily for a period of 2-5 weeks.

As discussed herein, the effective amount may be for example 2 to 40 g or 2 to 30 g or 2 to 20 g or 5 to 40 g or 5 to 30 g or 5 g to 20 g or 10 to 20 g of resistant potato starch, as discussed herein.

The invention will now be further elucidated and/or explained by way of examples. However, the invention is not necessarily limited to or by the examples.

Experiment 1

Effect of CG-induced colitis and RS on fecal consistency, local inflammation, histological structure, and microbiota composition and functional gene contents.

Fecal Score

No diarrhea was observed in the control and RS treatments, however, CG-induced colitis increased fecal score throughout the experimental period as shown in FIG. 1.

Local Inflammation

Figure 2:
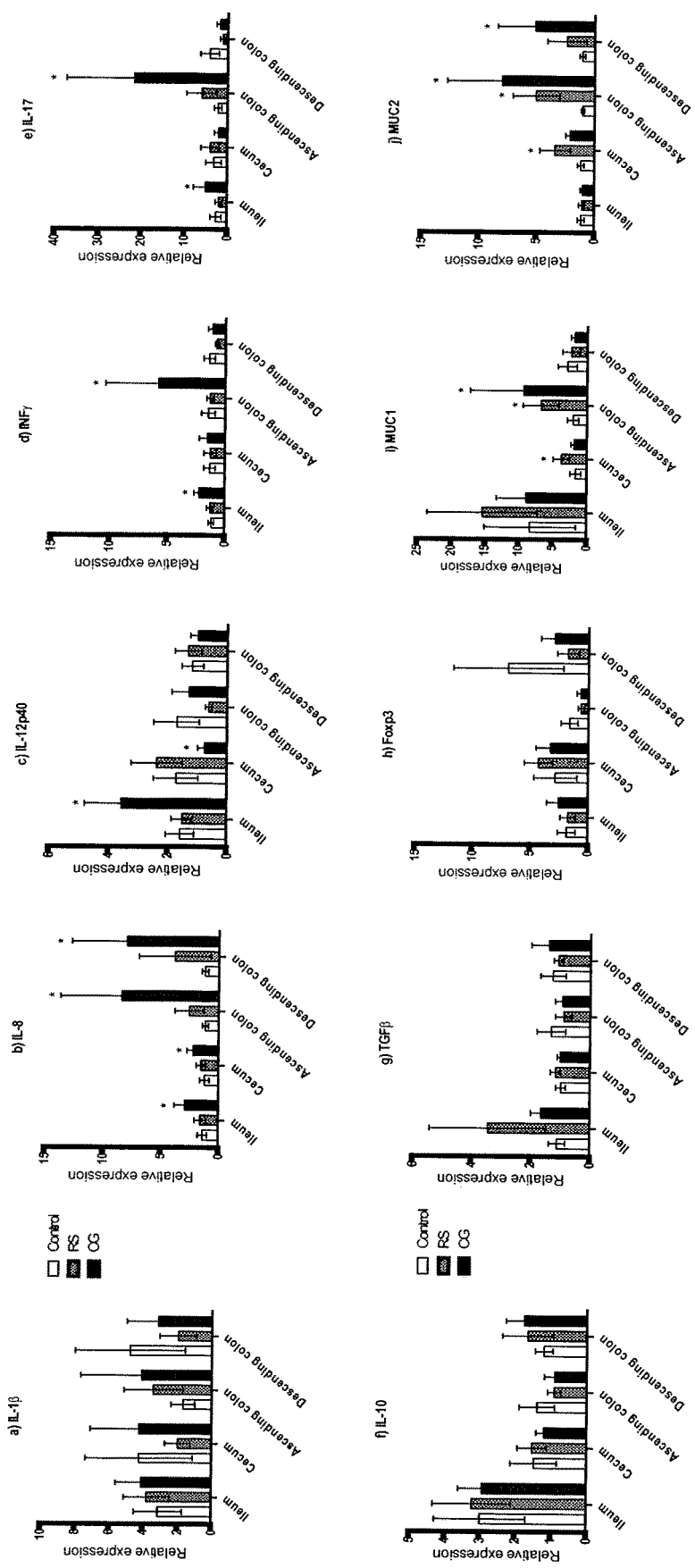
FIG. 2. Effect of degraded carrageenan gum (CG) and resistant starch (RS; MSPrebiotic) on local gene expression as determined by RT-PCR. CG was administered from d 1 of the experiment. Control=pigs received basal diet only, CG=pigs received 1% CG only in drinking water on daily basis, RS=pigs received basal diet and one scoop (10 g) of MSPrebiotic during the first 14 days of the experiment after which the amount of MSPrebiotic was adjusted to one scoop and half (15 g) until the end of the experimental period. All pigs were euthanized on day 40. The relative expression fold changes were determined using the ΔΔCt method with porcine β-actin as the housekeeping gene. * Designates a significant difference; $P \leq 0.05$.

Pro-inflammatory cytokines: IL-8, IL-12p40, IFN-γ, and IL-17 were measured in the ileum, cecum, ascending and descending colon as shown in FIG. 2 *a-e*. IL-1β was not significantly different among treatment groups across the intestinal segments. Compared to the control and RS treated pigs, CG-induced colitis significantly up-regulated IL-8 in all intestinal segments, as well as IFN-γ, and IL-17 in the ileum and ascending colon. IL-12p40 was only significantly upregulated in the ileum of colitic pigs but a down-regulation was observed in the cecum compared to the control and RS treated pigs. Expression of anti-inflammatory cytokines IL-10 and TGF-β as well as the regulatory cytokine Foxp3 were also tested, but no significant differences were observed across the intestinal segments as shown in FIG. 2 *f-h*. To further assess mucosal integrity, expression of MUC1 and MUC2 genes was determined as shown in FIG. 2 *i-j*. Both genes were up regulated in the cecum of RS group, and in the ascending colon of RS and CG treated pigs compared to the control. MUC2 was significantly lower in the descending colon of control pigs compared to CG.

Histological Structure in the Colon Tissue of Pigs with CG-Induced Colitis

The H&E staining analysis indicated that administration of CG markedly increased the severity of colitis compared to the control and RS pigs, in both the ascending and descending colon tissues as shown in FIG. 3 *a-d*. The lesions of the colon in the CG-treated group manifested mucosal erosion, loss of epithelial and goblet cells, and shortening and collapse of crypts.

Predicted Functional Pathways/Activities

Several pathways were enriched in the ileal mucosa-associated microbiota of the colitic pigs compared to the RS and control pigs. Specifically, biosynthesis of ansamycins, ascorbate and aldarate metabolism, pentose and glucuronate interconversions, phenylpropanoid biosynthesis, arachidonic metabolism, and retinol metabolism were enriched in the CG-treated pigs. Primary and secondary bile biosynthesis was enriched in the ileal microbiota of control pigs and there were no differences between the control and RS treated pigs.

Compared to the control, cecal mucosa-associated microbiota of the pigs exposed to CG colitis was enriched with several functional pathways including galactose metabolism, starch and sucrose metabolism, fructose and mannose metabolism, amino sugar and nucleotide sugar metabolism, alanine, aspartate and glutamate metabolism, peptidases, among other functional pathways. Very few pathways were significantly different between colitic and RS treated pigs in the cecum, whereas compared to the control, RS treated pigs were enriched with several pathways including peptidoglycan biosynthesis, amino sugar and nucleotide sugar metabolism, peptidases, one carbon pool by carbonate, and cyanoamino acid metabolism, among other pathways.

Most of the functional pathways in the ascending colon were significantly enriched in the colitic pigs, and in RS treated pigs when compared to the control pigs. However, there was no significantly different functional pathways between colitic and RS treated pigs. Methane metabolism, peptidoglycan biosynthesis, fructose and mannose metabolism, peptidases, amino sugar and nucleotide sugar metabolism, starch and sucrose metabolism, naphthalene degradation among other pathways were enriched in the CG treated pigs, whereas alanine, aspartate and glutamate metabolism, taurine and hypotaurine metabolism, streptomycin biosynthesis, peptidases, cyanoamino acid metabolism, sphigolipid metabolism, amino sugar and nucleotide sugar metabolism, starch and sucrose metabolism, among other functional pathways were enriched in the microbiota of RS treated pigs compared to the control. Only a few bacterial functional pathways were significantly enriched in the descending colon of colitic pigs compared to RS or the control pigs. In this case, cyanoamino acid metabolism, phenylpropanoid biosynthesis, and butirosin and neomycin biosynthesis were significantly enriched in the colitic pigs compared to the control, whereas only riboflavin metabolism was significantly enriched in the colitic pigs compared to RS treated pigs. On the other hand, valine, leucine and isoleucine degradation, fatty acid metabolism, limonene and pinene degradation, tryptophan metabolism, benzoate degradation, and phosphonate and phosphinate metabolism were enriched in the RS treated pigs compared to the colitic pigs.

Experiment 2: Inhibitory and Therapeutic Effects of Resistant Starch (RS; MSprebiotic) on Fecal Consistency, Local Inflammation, Histological Damage, and Microbiota Composition and Functional Gene Contents in Pigs with CG-Induced Colitis Fecal Score The protective and therapeutic effects of RS on fecal consistency are shown in FIG. 4. Therapeutic use of resistant starch after two weeks of colitis (RST) drastically reduced fecal score, however, after the introduction of colitis in the prevention group (RSP), there was a slow and gradual increase in the fecal score, although the score was still below that of CG group.

Local Pro- and Anti-Inflammatory Responses, and Gut Barrier Function.

Figure 5:
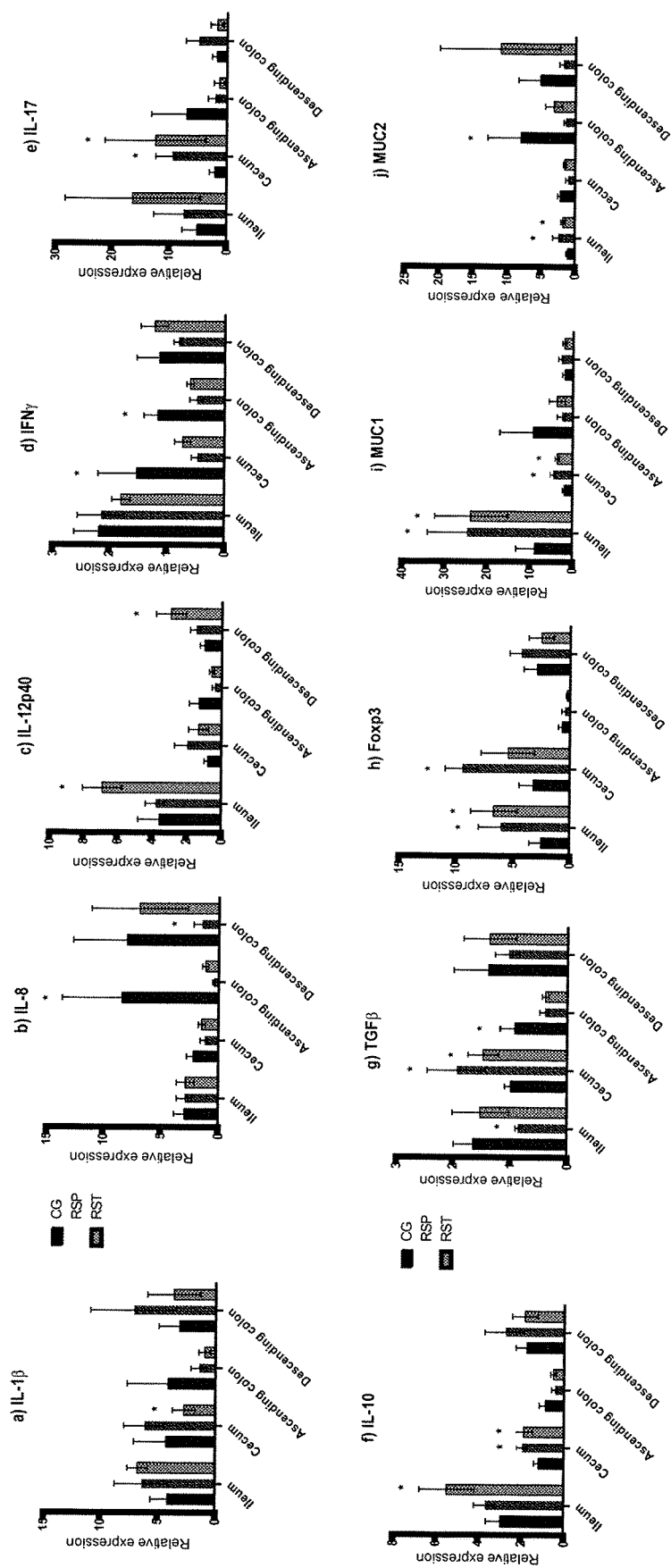
FIG. 5. Therapeutic or/and protective effect of resistant starch (RS; MSPrebiotic) on local gene expression as determined by RT-PCR in pigs exposed to degradeed carrageenan gum (CG)-induced colitis. CG was administered from d 1 of the experiment. Control=pigs received basal diet only, CG=pigs received 1% CG only in drinking water on daily basis, RSP=pigs received 10 g daily RS alone for the first 14 d of the study and CG was introduced at the start of d 15 until the end of the experimental period. Also starting from d 15 of the experiment, the amount of RS was adjusted to 15 g/d, RST=pigs received CG alone during the first 14 d of the experiment and RS was introduced (15 g) from 15th day of the study up to the end of the experimental period.

As shown in FIG. 5 *a-e*, inclusion of RS down regulated various pro-inflammatory cytokines including IL-1β in the cecum of RST group, IL-8 in the ascending colon of both RST and RSP, and in the descending colon of RSP group, and IFN-γ in the cecum and ascending colon of RSP and RST groups. However, IL-12p40 was up regulated in both the ileum and descending colon of the RST group, whereas IL-17 was up regulated in the cecum of both RSP and RST treatment groups. Expression of anti-inflammatory cytokines IL-10, transforming growth factor (TGF)-β and the regulatory forkhead box p3 (Foxp3) gene were also tested as shown in FIG. 5 *f-h*. IL-10 was up regulated in the ileum of RST group, both RST and RSP up-regulated IL-10 in the cecum, but a down regulation was observed in the ileum of RSP group, and in the ascending colon of both RSP and RST groups. Ileal Foxp3 was up regulated in both RST and RSP groups, but only RSP significantly up-regulated Foxp3 in the cecum. To further assess epithelial integrity, relative expression of the mucin genes, MUC1 and MUC2, was investigated as shown in FIG. 5 *i-j*. Compared to CG, RSP and RST up-regulated both genes in the ileum; however, only the expression of MUC1 was up-regulated in the cecum of RSP and RST treated pigs, but there was a down-regulation of MUC2 in the ascending colon of RSP and RST treated pigs.

Protective and Therapeutic Effect of MSPrebiotic on Histological Damage in the Colon Tissue of Pigs with CG-Induced Colitis.

Figure 6:
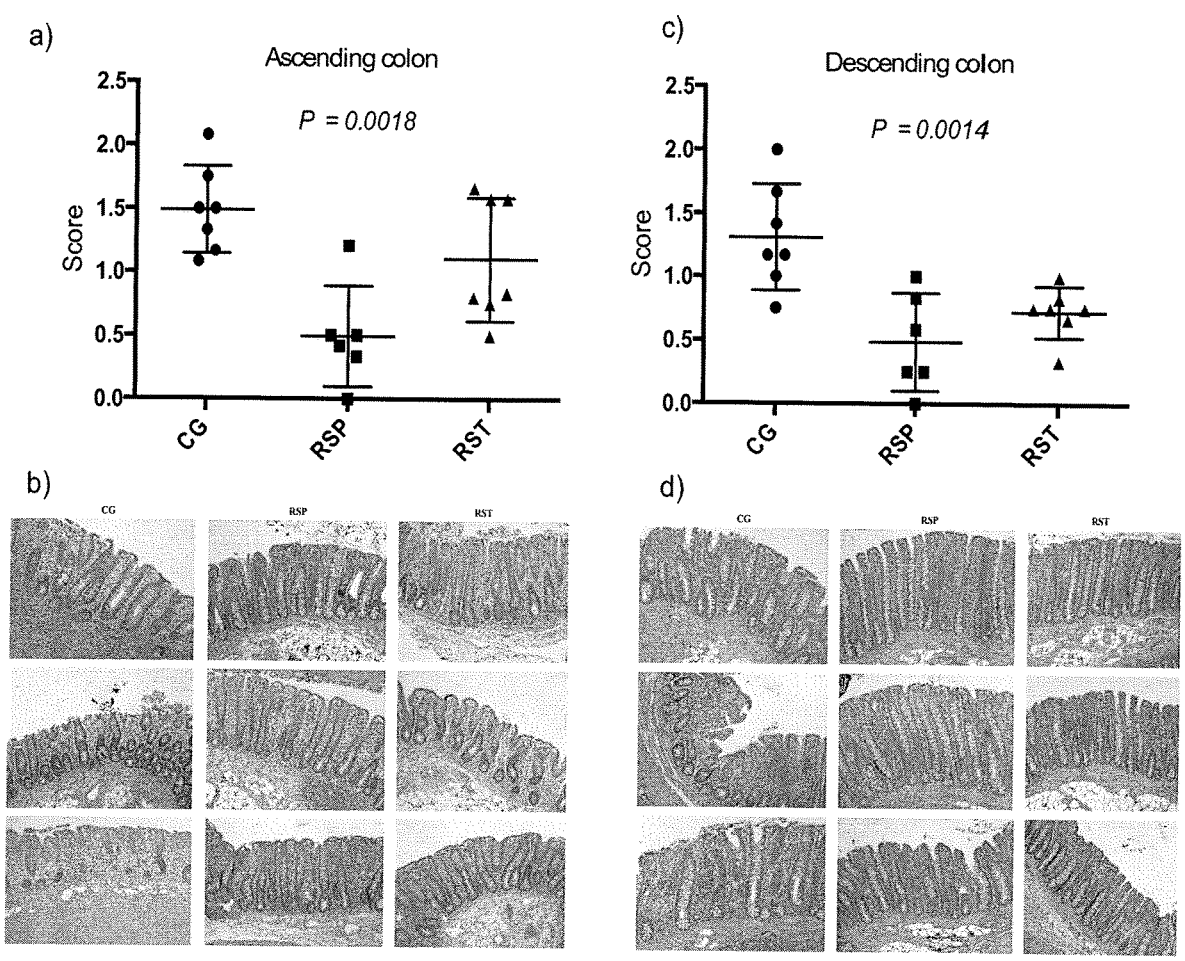
FIG. 6. Therapeutic or/and protective effect of resistant starch (RS; MSPrebiotic) on histological structure in pigs exposed to degraded carrageenan gum (CG)-induced colitis. a) and b) shows histological score and the extent of histological damage, respectively in the ascending colon. c) and d) shows the histological score and the extent of histological damage, respectively in the descending colon. CG was administered from d 1 of the experiment. Control=pigs received basal diet only, CG=pigs received 1% CG only in drinking water on daily basis, RSP=pigs received 10 g daily RS alone for the first 14 d of the study and CG was introduced at the start of d 15 until the end of the experimental period. Also starting from d 15 of the experiment, the amount of RS was adjusted to 15 g/d, RST=pigs received CG alone during the first 14 d of the experiment and RS was introduced (15 g) from 15th day of the study up to the end of the experimental period.

The inhibitory and therapeutic effects of RS on CG-induced colitis damage on the ascending and descending colon are shown in FIG. 6. Protective and therapeutic administration of resistant starch reduced colon lesions in CG-induced colitis; however, the therapeutic effects of RS on ascending colon were less prominent compared to the protective effects.

Bacterial Composition at the Phylum Level

Firmicutes, Bacteroidetes, Proteobacteria, and Spirochaetes were the most abundant and dominant phyla across the intestinal segments, whereas other phyla were less represented. No significant differences were observed between treatment groups across the intestinal segments.

Taxa Characterizing Treatment Groups within Tissue Sites.

Figure 7:
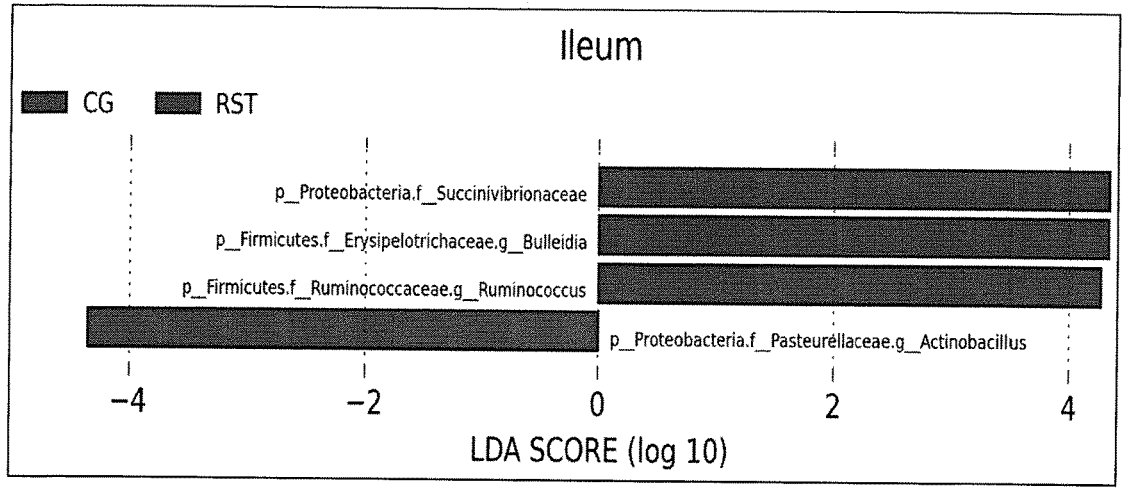
FIG. 7. Therapeutic or/and protective effect of resistant starch (RS; MSPrebiotic) on phylogenetic comparisons of ileal mucosa-associated microbiota in pigs exposed to degraded carrageenan gum (CG)-induced colitis. LEfSe was used to determine differentially abundant taxa in each treatment group. Color code represents specific treatment group and only variables that were significantly enriched in each treatment group are shown. There were no significant variables associated with the RSP group. CG was administered from d 1 of the experiment. Control=pigs received basal diet only, CG=pigs received 1% CG only in drinking water on daily basis, RSP=pigs received 10 g daily RS alone for the first 14 d of the study and CG was introduced at the start of d 15 until the end of the experimental period. Also starting from d 15 of the experiment, the amount of RS was adjusted to 15 g/d, RST=pigs received CG alone during the first 14 d of the experiment and RS was introduced (15 g) from 15th day of the study up to the end of the experimental period.

Ileum: The most differentially abundant bacterial taxa in CG pigs belong to phylum Proteobacteria, including genus *Actinobacillus*, whereas the RST treated pigs were characterized by taxa belonging to Proteobacteria and Firmicutes phyla, including genera *Bulleidia* and *Ruminococcus*, and clades of Succinivibrionaceae. No significant taxa were enriched in the RSP group as shown in FIG. 7.

Figure 8:
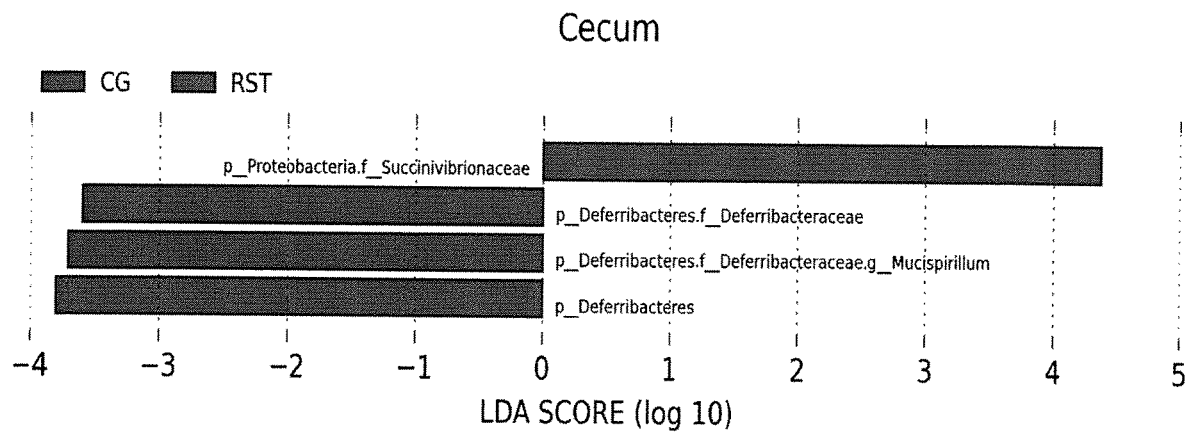
FIG. 8. Therapeutic or/and protective effect of resistant starch (RS; MSPrebiotic) on phylogenetic comparisons of cecal mucosa-associated microbiota in pigs exposed to degraded carrageenan gum (CG)-induced colitis. LEfSe was used to determine differentially abundant taxa in each treatment group. Color code represents specific treatment group and only variables that were significantly enriched in each treatment group are shown. There were no significant variables associated with the RSP group. CG was administered from d 1 of the experiment. Control=pigs received basal diet only, CG=pigs received 1% CG only in drinking water on daily basis, RSP=pigs received 10 g daily RS alone for the first 14 d of the study and CG was introduced at the start of d 15 until the end of the experimental period. Also starting from d 15 of the experiment, the amount of RS was adjusted to 15 g/d, RST=pigs received CG alone during the first 14 d of the experiment and RS was introduced (15 g) from 15th day of the study up to the end of the experimental period.

Cecum: The most differentially abundant bacterial taxa in colitic pigs belong to phylum Deferribacteres, including genus *Mucispirillum*, and clades of Deferribacteraceae, whereas RST pigs were only enriched with clades of Succinivibrionaceae, and no taxa were significantly associated with RSP compared to other groups as shown in FIG. 8.

Figure 9:
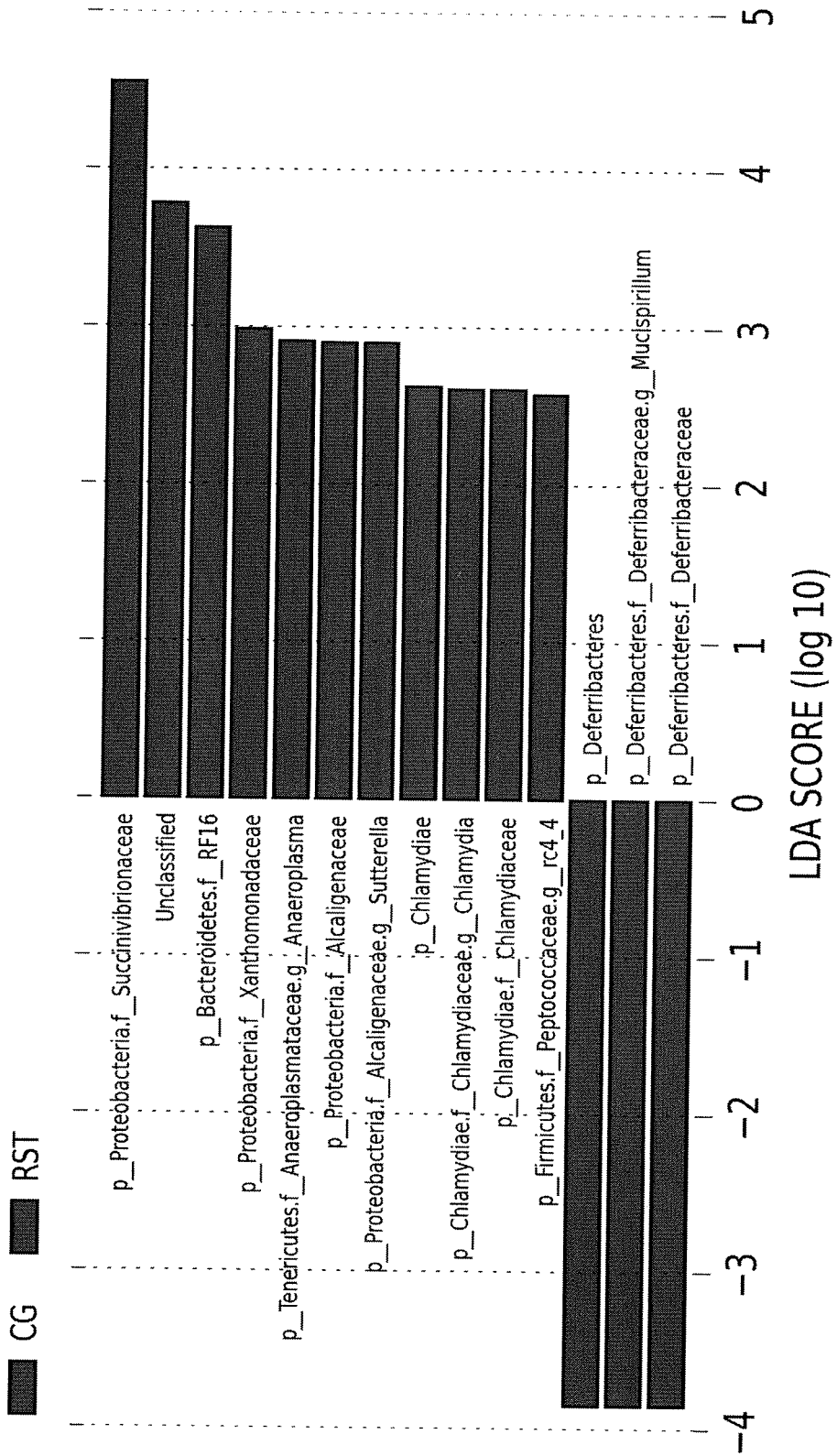
FIG. 9. Therapeutic or/and protective effect of resistant starch (RS; MSPrebiotic) on phylogenetic comparisons of ascending colon mucosa-associated microbiota in pigs exposed to degraded carrageenan gum (CG)-induced colitis. LEfSe was used to determine differentially abundant taxa in each treatment group. Color code represents specific treatment group and only variables that were significantly enriched in each treatment group are shown. There were no significant variables associated with the RSP group. CG was administered from d 1 of the experiment. Control=pigs received basal diet only, CG=pigs received 1% CG only in drinking water on daily basis, RSP=pigs received 10 g daily RS alone for the first 14 d of the study and CG was introduced at the start of d 15 until the end of the experimental period. Also starting from d 15 of the experiment, the amount of RS was adjusted to 15 g/d, RST=pigs received CG alone during the first 14 d of the experiment and RS was introduced (15 g) from 15th day of the study up to the end of the experimental period.

Ascending colon: CG pigs were largely characterized by clades within the phylum Deferribacteres, including genus *Mucispirillum*, and clades of Deferribacteraceae, whereas the RST group was enriched with members of phyla Proteobacteria, Bacteroidetes, Firmicutes, Tenericutes and Chlamydiae, including genera rc4_4, *Chlamydia*, Sutterella and Anaeroplasa, and clades of Succinivibrionaceae, RF16, Alcaligenaceae and Chlamydiaceae. No significant taxa were associated with RSP compared to other groups as shown in FIG. 9.

Figure 10:
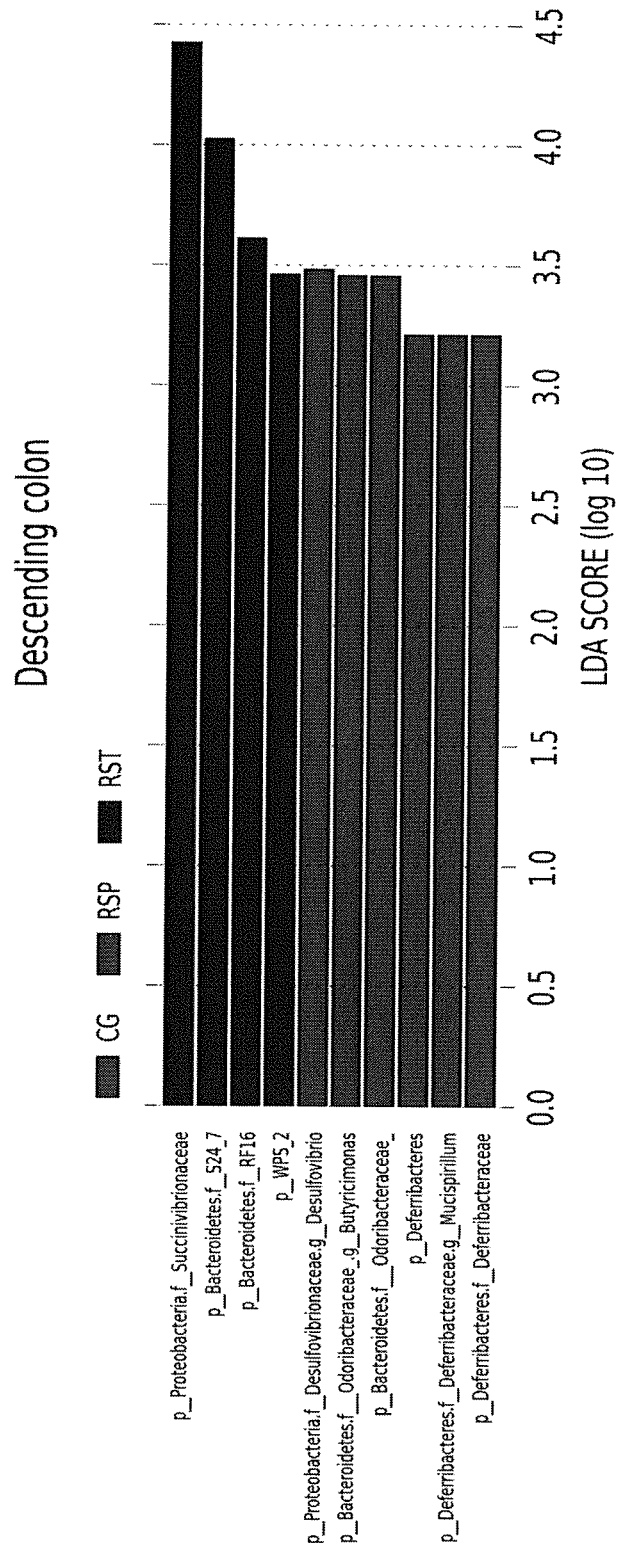
FIG. 10. Therapeutic or/and protective effect of resistant starch (RS; MSPrebiotic) on phylogenetic comparisons of descending colon mucosa-associated microbiota in pigs exposed to degraded carrageenan gum (CG)-induced colitis. LEfSe was used to determine differentially abundant taxa in each treatment group. Color code represents specific treatment group and only variables that were significantly enriched in each treatment group are shown. There were no significant variables associated with the RSP group. CG was administered from d 1 of the experiment. Control=pigs received basal diet only, CG=pigs received 1% CG only in drinking water on daily basis, RSP=pigs received 10 g daily RS alone for the first 14 d of the study and CG was introduced at the start of d 15 until the end of the experimental period. Also starting from d 15 of the experiment, the amount of RS was adjusted to 15 g/d, RST=pigs received CG alone during the first 14 d of the experiment and RS was introduced (15 g) from $15^{th}$ day of the study up to the end of the experimental period.

Descending colon: The most differentially abundant bacterial taxa in CG pigs belong to phyla Deferribacteres and Bacteroidetes including genera Butyricimonas and *Mucispirillum* and other unclassified members of Deferribacteraceae and Odoribacteraceae. RSP pigs were only enriched with genus *Desulfovibrio*, whereas RST was enriched with members of Proteobacteria, Bacteroidetes and WPS_2 including clades of Succinivibrionaceae, S24_7 and RF16 as shown in FIG. 10.

Predicted Functional Pathways/Activities

Several functional pathways, including retinol metabolism, inositol phosphate metabolism, and taurine and hypotaurine metabolism were significantly enriched in the ileal microbiota of CG group compared to the RSP group, and there were no significant differences between CG and RST. Likewise, few significant functional pathways were observed among treatment groups in the cecum and ascending colon. On the other hand, lipid acid metabolism was significantly enriched in the descending colon of RSP pigs, whereas secondary bile acid biosynthesis, biosynthesis of ansamycins, and sulfur metabolism were significantly enriched in the descending colon of CG treated pigs. In addition, several microbial functional pathways were significantly enriched in the descending colon of RST group compared to the CG group including penicillin and cephalosporin biosynthesis, geraniol degradation, caprolacta degradation, tryptophan metabolism, fatty acid metabolism, novobiocin biosynthesis, phenylalanine metabolism, lysine degradation, lipid biosynthesis proteins, among other pathways.

Materials and Methods

Animals

In a forty-day study, a total of 35 pigs [Durocx(YorkshirexLandrace)] weaned at 20±1 d (average 6 kg) were obtained from Glenlea research station, University of Manitoba, MB, Canada. Upon arrival, the piglets were housed in group pens for 3 days after which they were randomly assigned to experimental treatments (based on body weight) with 7 pigs per treatment, moved to individual pens, and allowed 3 more days for acclimatization before the start of experimental procedures. The Pigs were housed in temperature-controlled rooms within T. K. Cheung Center for Animal Science Research, University of Manitoba, Winnipeg, MB, Canada. Room temperatures were maintained at 30° C. during wk 1 and the temperatures were reduced by 1° C. every week, with a 16 h lighting system. All pigs had ad libitum access to water and basal diet in mash form formulated to meet or exceed the national research council (NRC, 2012) recommendations for a 7 to 11 kg and 11 to 25 kg pigs.

Resistant Starch

Potato resistant starch (RS; MSPrebiotic) in powder form was provided by the McPharma Neutraceuticals, Carberry, Manitoba, Canada, in pouches of 454 g each. Each pouch contained a 10 g scoop. The RS was mixed with a small amount of feed every morning and pigs were allowed to finish the RS-containing feed first.

Diet and Experimental Treatments

A basal corn-soybean-based diet formulated to meet or exceed NRC (2012) nutrient recommendations for a 7 to 11 kg pig, and for an 11 to 25 kg pig was used. The 40-day study was divided into two experiments. Pigs were weighed and randomly assigned to the treatment groups with one pig per pen and 7 replicate pens per treatment.

Severity of diarrhea was characterized using the fecal consistency scoring system described by Marquardt et al. (Marquardt et al., 1999); (0, normal; 1, soft feces; 2, mild diarrhea; 3, severe diarrhea). The scoring was done daily, and each week's average score was used for statistical analysis.

Digesta and Tissue Sampling

At the end of the study (d 40), blood was collected from the jugular vein and all pigs were sedated by intramuscular injection of Ketamine:Xylazine (20:2 mg/kg BW) and euthanized by an intracardiac injection of 110 mg/kg BW sodium pentobarbital (Bimeda-MTC Animal Health Inc., Cambridge, ON, Canada). The abdominal cavity was opened from sternum to pubis to expose the gastrointestinal tract without damaging the wall of the digestive tract. The small intestine was stripped free of its mesentery and feces, ileal, cecal and colon digesta samples were obtained, and transferred to sterile sample containers. The fecal and digesta samples were used for determination of pH, and immediately 0.1N HCl was added (1:1 v/w), and the samples were transferred to −20° C. for later analysis of volatile fatty acids (VFA). Tissue samples (three segments) were collected from the ileum, cecum, ascending, and descending colon, flushed with sterile saline to remove excess lumen contents, and used for histological analysis, microbial analyses, and for local gene expression. Samples for microbial analysis and gene expression were immediately frozen in liquid nitrogen and transferred to −80° C. until use.

Analysis of pH and Volatile Fatty Acids (VFA).

pH was measured immediately after digesta collection using an Accumet Basic 15 pH meter (Fisher Scientific, Fairlawn, N.J.) equipped with a Sensorex 450C Flat Surface Combination pH/Reference Electrode (Sensorex, Stanton, Calif.), which was standardized with certified pH 4 and 7 buffer solutions, whereas volatile fatty acids were determined using gas chromatography (Bhandari et al., 2007).

Histological Examination

Immediately following sacrifice, sections of the intestinal tissue samples were removed and cleaned in saline solution to remove luminal contents. The tissue samples were then placed into 10% buffered formalin and kept in formalin for 2-3 days. Tissues were embedded in paraffin then sections stained with hemotoxylin and eosin (H&E) prior to microscopic observation. Colonic damage was scored based on a published scoring system that considers architectural derangements, goblet cell depletion, edema/ulceration and degree of inflammatory cell infiltration (Cooper et al., 1993)

RNA Isolation and Analysis of Local Gene Expression by Reverse Transcriptase Quantitative Real Time PCR (RT-qPCR)

Real time RT-qPCR analysis was used to measure gene expression of various biomarkers in the ileum, cecum, ascending and descending colon tissue samples. Total RNA was extracted from the tissue samples and purified using MagMax Total RNA Isolation Kit (Life Technologies, CA, USA), according to the manufacturer's instructions. Reverse transcriptase cDNA synthesis was done using superscript II RT and random primers (Invitrogen), following the manufacturer's protocol. Real-time PCR was performed using SsoFast EvaGreen Supermix (Bio Rad Laboratories, Inc). The real-time PCR amplification was run on a LightCycler (Bio-Rad Laboratories, Inc) using the following conditions: enzyme activation for 3 min at 95° C., followed by 40 cycles of denaturation for 10 s at 95° C. Porcine primers were designed using Primer 3 v.0.4.0 as used in a previous study (Lee et al., 2009) and are shown in Table 1. The threshold cycle ($C_T$) was determined by CFX manager software, and the relative mRNA expression of the genes was calculated using the $\Delta\Delta Ct$ method, with porcine β-actin as the housekeeping gene.

DNA Extraction and Quality Control.

DNA was extracted from tissue samples using ZR DNA extraction kits as described previously (Munyaka et al 2016 a, b).

Real Time PCR Determination of 16S rRNA Gene Copy Number: Absolute Quantification.

To determine the 16S rRNA gene copy numbers in tissue DNA samples, the universal primers F338 primer for forward primer and R806 were used (Caporaso et al., 2012). The real-time PCR amplification was run on a LightCycler (Bio Rad Laboratories, Inc), and the threshold cycle (C T) was determined by CFX manager software. The PCR was performed in triplicate, and each reaction mixture was prepared using the SsoFast Eva Green Supermix (Bio Rad Laboratories, Inc) in a total volume of 20 µl: 6.4 µl PCR-grade water, 0.8 µl of each primer (final concentration 0.5 µM), 10 µl Eva green master mix, and 2.0 µl template DNA. The thermal cycling protocol was as follows: enzyme activation for 3 min at 95° C. followed by 40 cycles of 10 s at 95° C., and 30 s at 58° C., and the fluorescence signal was measured at the end of each extension step.

Linear Discriminant Analysis with Effect Size (Lefse) Analysis

LEfSe (Segata et al., 2011) was used to identify overrepresented taxa between pigs with CG-induced colitis and non-colitic pigs (control and RS), and between pigs with CG-induced colitis and those with RS as a protective (RSP) or therapeutic (RST) measure.

Prediction of Functional Metagenomics

The open source software PICRUSt (Phylogenetic Investigation of Communities by Reconstruction of Unobserved States; v. 1.0.0-dev) was used to predict the functional capacity of the microbiome using 16S rRNA gene sequencing data and the Greengenes (v. 13.5) reference database (DeSantis et al., 2006), as described in manuscript I (Munyaka et al., 2016 a, b).

Statistical Analysis.

For the volatile fatty acids, pH, alpha-diversity and phylum data, the effect of treatment was evaluated in a completely randomized design and the data was subjected to ANOVA using the PROC MIXED procedure of SAS (SAS 9.3). Differences between means were determined using Pdiff and the UNIVARIATE procedure of SAS was used to test the normality of residuals. The differences between treatments were considered significant at $P<0.05$. One-way ANOVA followed by Tukey's multiple-comparison test was used to compare the histological scores and local inflammatory markers between treatment groups using Graphpad Prism 5.0c (Graphpad Prism, La Jolla, Calif., USA). The significance level was adjusted at 0.05.

The scope of the claims should not be limited by the preferred embodiments set forth in the examples but should be given the broadest interpretation consistent with the description as a whole.

REFERENCES

Asp, N. G. (1987). Definition and analysis of dietary fibre. Scand J Gastroenterol Suppl 129, 16-20.

Bassaganya-Riera, J., Diguardo, M., Viladomiu, M., De Horna, A., Sanchez, S., Einerhand, A. W. C., Sanders, L., and Hontecillas, R. (2011). Soluble Fibers and Resistant Starch Ameliorate Disease Activity in Interleukin-10-Deficient Mice with Inflammatory Bowel Disease. Journal of Nutrition 141, 1318-1325. doi: 10.3945/jn.111.139022.

Bergstrom, K. S., and Xia, L. (2013). Mucin-type 0-glycans and their roles in intestinal homeostasis. Glycobiology 23, 1026-1037. doi: 10.1093/glycob/cwt045.

Bhandari, S. K., Ominski, K. H., Wittenberg, K. M., and Plaizier, J. C. (2007). Effects of chop length of alfalfa and corn silage on milk production and rumen fermentation of dairy cows. J Dairy Sci 90, 2355-2366. doi: 10.3168/jds.2006-609.

Boltin, D., Perets, T. T., Vilkin, A., and Niv, Y. (2013). Mucin function in inflammatory bowel disease: an update. J Clin Gastroenterol 47, 106-111. doi: 10.1097/MCG.0b013e3182688e73.

Butzner, J. D., Parmar, R., Bell, C. J., and Dalai, V. (1996). Butyrate enema therapy stimulates mucosal repair in experimental colitis in the rat. Gut 38, 568-573.

Caporaso, J. G., Lauber, C. L., Walters, W. A., Berg-Lyons, D., Huntley, J., Fierer, N., Owens, S. M., Betley, J., Fraser, L., Bauer, M., Gormley, N., Gilbert, J. A., Smith, G., and Knight, R. (2012). Ultra-high-throughput microbial community analysis on the Illumina HiSeq and MiSeq platforms. ISME J 6, 1621-1624. doi: 10.1038/ismej.2012.8.

Cooper, H. S., Murthy, S. N. S., Sedergran, D. J., and Shah, R. S. (1993). Clinicopathologic study of dextran sulfate sodium experimental murine colitis. Laboratory Investigation 69, 238-250.

Cummings, J. H., and Englyst, H. N. (1987). Fermentation in the human large intestine and the available substrates. Am J Clin Nutr 45, 1243-1255.

Cummings, J. H., Roberfroid, M. B., Andersson, H., Barth, C., Ferro-Luzzi, A., Ghoos, Y., Gibney, M., Hermansen, K., James, W. P., Korver, O., Lairon, D., Pascal, G., and Voragen, A. G. (1997). A new look at dietary carbohydrate: chemistry, physiology and health. Paris Carbohydrate Group. Eur J Clin Nutr 51, 417-423.

Daig, R., Andus, T., Aschenbrenner, E., Falk, W., Scholmerich, J., and Gross, V. (1996). Increased interleukin 8 expression in the colon mucosa of patients with inflammatory bowel disease. Gut 38, 216-222. doi: DOI 10.1136/gut.38.2.216.

Darfeuille-Michaud, A., Boudeau, J., Bulois, P., Neut, C., Glasser, A. L., Barnich, N., Bringer, M. A., Swidsinski, A., Beaugerie, L., and Colombel, J. F. (2004). High prevalence of adherent-invasive *Escherichia coli* associated with ileal mucosa in Crohn's disease. Gastroenterology 127, 412-421.

Desantis, T. Z., Hugenholtz, P., Larsen, N., Rojas, M., Brodie, E. L., Keller, K., Huber, T., Dalevi, D., Hu, P., and Andersen, G. L. (2006). Greengenes, a chimera-checked 16S rRNA gene database and workbench compatible with ARB. Applied and Environmental Microbiology 72, 5069-5072. doi: Doi 10.1128/Aem.03006-05.

Dorofeyev, A. E., Vasilenko, I. V., Rassokhina, O. A., and Kondratiuk, R. B. (2013). Mucosal barrier in ulcerative colitis and Crohn's disease. Gastroenterol Res Pract 2013, 431231. doi: 10.1155/2013/431231.

Egger, B., Bajaj-Elliott, M., Macdonald, T. T., Inglin, R., Eysselein, V. E., and Buchler, M. W. (2000). Characterisation of acute murine dextran sodium sulphate colitis: Cytokine profile and dose dependency. Digestion 62, 240-248. doi: Doi 10.1159/000007822.

Eken, A., Singh, A. K., Treuting, P. M., and Oukka, M. (2014). IL-23R+ innate lymphoid cells induce colitis via interleukin-22-dependent mechanism. Mucosal Immunol 7, 143-154. doi: 10.1038/mi.2013.33.

Fujino, S., Andoh, A., Bamba, S., Ogawa, A., Hata, K., Araki, Y., Bamba, T., and Fujiyama, Y. (2003). Increased expression of interleukin 17 in inflammatory bowel disease. Gut 52, 65-70. doi: DOI 10.1136/gut.52.1.65.

Fuss, I. J. (2011). IL-17: intestinal effector or protector? Mucosal Immunology 4, 366-367. doi: 10.1038/mi.2011.24.

Ghia, J. E., Blennerhassett, P., and Collins, S. M. (2007a). Vagus nerve integrity and experimental colitis. Am J Physiol Gastrointest Liver Physiol 293, G560-567. doi: 10.1152/ajpgi.00098.2007.

Ghia, J. E., Blennerhassett, P., EI-Sharkawy, R. T., and Collins, S. M. (2007b). The protective effect of the vagus nerve in a murine model of chronic relapsing colitis. Am J Physiol Gastrointest Liver Physiol 293, G711-718. doi: 10.1152/ajpgi.00240.2007.

Ghia, J. E., Li, N., Wang, H. Q., Collins, M., Deng, Y. K., EI-Sharkawy, R. T., Cote, F., Mallet, J., and Khan, W. I. (2009). Serotonin Has a Key Role in Pathogenesis of Experimental Colitis. Gastroenterology 137, 1649-1660. doi: Doi 10.1053/J. Gastro.2009.08.041.

Haenen, D., Da Silva, C. S., Zhang, J., Koopmans, S. J., Bosch, G., Vervoort, J., Gerrits, W. J. J., Kemp, B., Smidt, H., Muller, M., and Hooiveld, G. J. E. J. (2013). Resistant Starch Induces Catabolic but Suppresses Immune and Cell Division Pathways and Changes the Microbiome in the Proximal Colon of Male Pigs. Journal of Nutrition 143, 1889-1898. doi: 10.3945/jn.113.182154.

Higgins, J. A., and Brown, I. L. (2013). Resistant starch: a promising dietary agent for the prevention/treatment of inflammatory bowel disease and bowel cancer. Curr Opin Gastroenterol 29, 190-194. doi: 10.1097/MOG.0b013e32835b9aa3.

Hoebler, C., Gaudier, E., De Coppet, P., Rival, M., and Cherbut, C. (2006). MUC genes are differently expressed during onset and maintenance of inflammation in dextran sodium sulfate-treated mice. Dig Dis Sci 51, 381-389. doi: 10.1007/s10620-006-3142-y.

Hu, Y., Le Leu, R. K., Christophersen, C. T., Somashekar, R., Conlon, M. A., Meng, X. Q., Winter, J. M., Woodman, R. J., Mckinnon, R., and Young, G. P. (2016). Manipulation of the gut microbiota using resistant starch is associated with protection against colitis-associated colorectal cancer in rats. Carcinogenesis 37, 366-375. doi: 10.1093/carcin/bgw019.

Jiang, H., Przybyszewski, J., Mitra, D., Becker, C., Brehm-Stecher, B., Tentinger, A., and Macdonald, R. S. (2011). Soy protein diet, but not *Lactobacillus rhamnosus* GG, decreases mucin-1, trefoil factor-3, and tumor necrosis factor-alpha in colon of dextran sodium sulfate-treated C57BL/6 mice. J Nutr 141, 1239-1246. doi: 10.3945/jn.110.137414.

Johansson, M. E. V., Phillipson, M., Petersson, J., Velcich, A., Holm, L., and Hansson, G. C. (2008). The inner of the two Muc2 mucin-dependent mucus layers in colon is devoid of bacteria. Proceedings of the National Academy of Sciences of the United States of America 105, 15064-15069. doi: 10.1073/pnas.0803124105.

Kotlowski, R., Bernstein, C. N., Sepehri, S., and Krause, D. O. (2007). High prevalence of *Escherichia coli* belonging to the B2+D phylogenetic group in inflammatory bowel disease. Gut 56, 669-675. doi: 10.1136/gut.2006.099796.

Kwon, K. H., Murakami, A., Tanaka, T., and Ohigashi, H. (2005). Dietary rutin, but not its aglycone quercetin, ameliorates dextran sulfate sodium-induced experimental colitis in mice: attenuation of pro-inflammatory gene expression. Biochem Pharmacol 69, 395-406. doi: 10.1016/j.bcp.2004.10.015.

Laroui, H., Ingersoll, S. A., Liu, H. C., Baker, M. T., Ayyadurai, S., Charania, M. A., Laroui, F., Yan, Y., Sitaraman, S. V., and Merlin, D. (2012). Dextran sodium sulfate (DSS) induces colitis in mice by forming nano-lipocomplexes with medium-chain-length fatty acids in the colon. PLoS One 7, e32084. doi: 10.1371/journal.pone.0032084.

Le Leu, R. K., Young, G. P., Hu, Y., Winter, J., and Conlon, M. A. (2013). Dietary red meat aggravates dextran sulfate sodium-induced colitis in mice whereas resistant starch attenuates inflammation. Dig Dis Sci 58, 3475-3482. doi: 10.1007/s10620-013-2844-1

Lee, M., Kovacs-Nolan, J., Yang, C., Archbold, T., Fan, M. Z., and Mine, Y. (2009). Hen egg lysozyme attenuates inflammation and modulates local gene expression in a porcine model of dextran sodium sulfate (DSS)-induced colitis. J Agric Food Chem 57, 2233-2240. doi: 10.1021/jf803133b.

Lupp, C., Robertson, M. L., Wickham, M. E., Sekirov, I., Champion, 01., Gaynor, E. C., and Finlay, B. B. (2007). Host-mediated inflammation disrupts the intestinal microbiota and promotes the Overgrowth of Enterobacteriaceae. Cell Host & Microbe 2, 119-129. doi: Doi 10.1016/J. Chom.2007.06.010.

Marquardt, R. R., Jin, L. Z., Kim, J. W., Fang, L., Frohlich, A. A., and Baidoo, S. K. (1999). Passive protective effect of egg-yolk antibodies against enterotoxigenic *Escherichia coli* K88+ infection in neonatal and early-weaned piglets. Fems Immunology and Medical Microbiology 23, 283-288. doi: Doi 10.1016/S0928-8244(98)00147-3.

Mcguckin, M. A., Eh, R., Simms, L. A., Florin, T. H. J., and Radford-Smith, G. (2009). Intestinal Barrier Dysfunction in Inflammatory Bowel Diseases. Inflammatory Bowel Diseases 15, 100-113. doi: 10.1002/ibd.20539.

Munyaka, P. M., Eissa, N., Bernstein, C. N., Khafipour, E., and Ghia, J. E. (2015). Antepartum Antibiotic Treatment Increases Offspring Susceptibility to Experimental Colitis: A Role of the Gut Microbiota. PLoS One 10, e0142536. doi: 10.1371/journal.pone.0142536.

Munyaka, P. M., Rabbi, M. F., Khafipour, E., and Ghia, J. E. (2016a). Acute dextran sulfate sodium (DSS)-induced colitis promotes gut microbial dysbiosis in mice. J Basic Microbiol. doi: 10.1002/jobm.201500726.

Munyaka, P. M., Sepehri, S., Ghia, J. E., and Khafipour, E. (2016b). Carrageenan Gum and Adherent Invasive *Escherichia coli* in a Piglet Model of Inflammatory Bowel Disease: Impact on Intestinal Mucosa-associated Microbiota. Front Microbiol 7, 462. doi: 10.3389/fmicb.2016.00462.

Mylonaki, M., Rayment, N. B., Rampton, D. S., Hudspith, B. N., and Brostoff, J. (2005). Molecular characterization of rectal mucosaassociated bacterial flora in inflammatory bowel disease. Infamm Bowel Dis 11, 481-487.

Nielsen, O. H., Rudiger, N., Gaustadnes, M., and Horn, T. (1997). Intestinal interleukin-8 concentration and gene expression in inflammatory bowel disease. Scandinavian Journal of Gastroenterology 32, 1028-1034. doi: Doi 10.3109/00365529709011220.

NRC (2012). Nutrient Requirements of swine. Washington, D.C.: Natl. Acad. Press.

O'connor, W., Kamanaka, M., Booth, C. J., Town, T., Nakae, S., Iwakura, Y., Kolls, J. K., and Flavell, R. A. (2009). A protective function for interleukin 17A in T cell-mediated intestinal inflammation. Nature Immunology 10, 603-U665. doi: 10.1038/ni.1736.

Panwala, C. M., Jones, J. C., and Viney, J. L. (1998). A novel model of inflammatory bowel disease: Mice deficient for the multiple drug resistance gene, mdr1a, spontaneously develop colitis. Journal of Immunology 161, 5733-5744.

Pastorelli, L., De Salvo, C., Mercado, J. R., Vecchi, M., and Pizarro, T. T. (2013). Central role of the gut epithelial barrier in the pathogenesis of chronic intestinal inflammation: lessons learned from animal models and human genetics. Front Immunol 4, 280. doi: 10.3389/fimmu.2013.00280.

Pizarro, T. T., Arseneau, K. O., Bamias, G., and Cominelli, F. (2003). Mouse models for the study of Crohn's disease. Trends in Molecular Medicine 9, 218-222. doi: 10.1016/s1471-4914(03)00052-2

Rabbi, M. F., Labis, B., Metz-Boutigue, M. H., Bernstein, C. N., and Ghia, J. E. (2014). Catestatin decreases macrophage function in two mouse models of experimental colitis. Biochem Pharmacol 89, 386-398. doi: 10.1016/j.bcp.2014.03.003.

Sartor, R. B. (2006). Mechanisms of disease: pathogenesis of Crohn's disease and ulcerative colitis. Nature Clinical Practice Gastroenterology & Hepatology 3, 390-407. doi: 10.1038/ncpgasthep0528.

Sellon, R. K., Tonkonogy, S., Schultz, M., Dieleman, L. A., Grenther, W., Balish, E., Rennick, D. M., and Sartor, R. B. (1998). Resident enteric bacteria are necessary for development of spontaneous colitis and immune system activation in interleukin-10-deficient mice. Infect Immun 66, 5224-5231.

Schuppler, M., Lotzsch, K., Waidmann, M., and Autenrieth, I. B. (2004). An Abundance of *Escherichia coli* Is Harbored by the Mucosa-Associated Bacterial Flora of Interleukin-2-Deficient Mice. Infection and Immunity 72, 1983-1990. doi: 10.1128/iai.72.4.1983-1990.2004.

Segata, N., Izard, J., Waldron, L., Gevers, D., Miropolsky, L., Garrett, W. S., and Huttenhower, C. (2011). Metagenomic biomarker discovery and explanation. Genome Biol 12, R60. doi: 10.1186/gb-2011-12-6-r60.

Sepehri, S., Khafipour, E., Bernstein, C. N., Coombes, B. K., Pilar, A. V., Karmali, M., Ziebell, K., and Krause, D. O. (2011). Characterization of *Escherichia coli* isolated from gut biopsies of newly diagnosed patients with inflammatory bowel disease. Inflamm Bowel Dis 17, 1451-1463. doi: 10.1002/ibd.21509.

Shah, S. A., Simpson, S. J., Brown, L. F., Comiskey, M., De Jong, Y. P., Allen, D., and Terhorst, C. (1998). Development of colonic adenocarcinomas in a mouse model of ulcerative colitis. Inflammatory Bowel Diseases 4, 196-202.

Tai, E. K., Wu, W. K., Wong, H. P., Lam, E. K., Yu, L., and Cho, C. H. (2007). A new role for cathelicidin in ulcerative colitis in mice. Exp Biol Med (Maywood) 232, 799-808.

Topping, D. L., and Clifton, P. M. (2001). Short-chain fatty acids and human colonic function: roles of resistant starch and nonstarch polysaccharides. Physiol Rev 81, 1031-1064.

Van Der Sluis, M., De Koning, B. A., De Bruijn, A. C., Velcich, A., Meijerink, J. P., Van Goudoever, J. B., Buller, H. A., Dekker, J., Van Seuningen, I., Renes, I. B., and Einerhand, A. W. (2006). Muc2-deficient mice spontaneously develop colitis, indicating that MUC2 is critical for colonic protection. Gastroenterology 131, 117-129. doi: 10.1053/j.gastro.2006.04.020.

Wirtz, S., Neufert, C., Weigmann, B., and Neurath, M. F. (2007). Chemically induced mouse models of intestinal inflammation. Nature Protocols 2, 541-546. doi: 10.1038/nprot.2007.41.

Wright, E. K., Kamm, M. A., Teo, S. M., Inouye, M., Wagner, J., and Kirkwood, C. D. (2015). Recent advances in characterizing the gastrointestinal microbiome in Crohn's disease: a systematic review. Inflamm Bowel Dis 21, 1219-1228. doi: 10.1097/MIB.0000000000000382.

Xenoulis, P. G., Palculict, B., Allenspach, K., Steiner, J. M., Van House, A. M., and Suchodolski, J. S. (2008). Molecular-phylogenetic characterization of microbial communities imbalances in the small intestine of dogs with inflammatory bowel disease. FEMS Microbiol Ecol 66, 579-589. doi: 10.1111/j.1574-6941.2008.00556.x.

Yang, X. X. O., Chang, S. H., Park, H., Nurieva, R., Shah, B., Acero, L., Wang, Y. H., Schluns, K. S., Broaddus, R. R., Zhu, Z., and Dong, C. (2008). Regulation of inflammatory responses by IL-17F. Journal of Experimental Medicine 205, 1063-1075. doi: 10.1084/jem.20071978.

TABLE 1

Porcine primers used for RT-PCR

| Gene | Forward primer (5'-3') | Reverse primer (5'-3') |
|---|---|---|
| β-actin | GGATGCAGAAGGAGATCACG (SEQ ID No: 1) | ATCTGCTGGAAGGTGGACAG (SEQ ID No: 2) |
| IL-8 | TGGCAGTTTTCCTGCTTTCT (SEQ ID No: 3) | CAGTGGGGTCCACTCTCAAT (SEQ ID No: 4) |

TABLE 1-continued

Porcine primers used for RT-PCR

| Gene | Forward primer (5'-3') | Reverse primer (5'-3') |
|---|---|---|
| IFN-γ | CCATTCAAAGGAGCATGGAT (SEQ ID No: 5) | GAGTTCACTGATGGCTTTGC (SEQ ID No: 6) |
| IL-1β | CAAAGGCCGCCAAGATATAA (SEQ ID No: 7) | GAAATTCAGGCAGCAACAT (SEQ ID No: 8) |
| IL-17 | TCATGATCCCACAAAGTCCA (SEQ ID No: 9) | AGTCCATGGTGAGGTGAAGC (SEQ ID No: 10) |
| IL-10 | TGATGGGGAGGATATCAAGG (SEQ ID No: 11) | TGGAGCTTGCTAAAGGCACT (SEQ ID No: 12) |
| TGF-β | CGAGCCCTGGATACCAACTA (SEQ ID No: 13) | AGGCTCCAGATGTAGGGACA (SEQ ID No: 14) |
| IL-12p | TTTCAGACCCGACGAACTCT (SEQ ID No: 15) | CATTGGGGTACCAGTCCAAC (SEQ ID No: 16) |
| Foxp3 | CTGACAAGGGTTCCTGCTGT (SEQ ID No: 17) | GAAATCTGGGAACGTGCTGT (SEQ ID No: 18) |
| MUC1 | ACCAAGTCCCCTAACCCATC (SEQ ID No: 19) | TTGGAATTTTCCAGGCAGTC (SEQ ID No: 20) |
| MUC2 | ACCCGCACTATGTCACCTTC (SEQ ID No: 21) | GGGATCGCAGTGGTAGTTGT (SEQ ID No: 22) |

The invention claimed is:

1. A method of treating Inflammatory Bowel disease in an individual suffering from a flare of ulcerative colitis comprising administering to said individual an effective amount of an unmodified potato starch that is at least 60% resistant starch, administering the effective amount until at least one symptom associated with the flare of ulcerative colitis is improved and then stopping administering the unmodified potato starch that is at least 60% resistant starch, with the proviso that the individual has not been administered a regimen of unmodified potato starch that is at least 60% resistant starch immediately prior to the flare of ulcerative colitis.

2. The method according to claim 1 wherein the effective amount of the unmodified potato starch that is at least 60% resistant starch is administered to the individual on a schedule or regimen.

3. The method according to claim 2 wherein the schedule or regimen is daily administration for a period of time.

4. The method according to claim 3 wherein the period of time is daily for about two weeks to about five weeks.

5. The method according to claim 1 wherein the symptom is diarrhea.

6. The method according to claim 1 wherein the unmodified potato starch that is at least 60% resistant starch has not been administered to the individual for at least two weeks prior to the flare of ulcerative colitis.

* * * * *

SEQUENCE LISTING

<160> NUMBER OF SEQ ID NOS: 22

<210> SEQ ID NO 1
<211> LENGTH: 20
<212> TYPE: DNA
<213> ORGANISM: artificial
<220> FEATURE:
<223> OTHER INFORMATION: PCR forward primer for porcine B-actin

<400> SEQUENCE: 1
ggatgcagaa ggagatcacg                20

<210> SEQ ID NO 2
<211> LENGTH: 20
<212> TYPE: DNA
<213> ORGANISM: artificial
<220> FEATURE:
<223> OTHER INFORMATION: PCR reverse primer for porcine B-actin

<400> SEQUENCE: 2
atctgctgga aggtggacag                20

<210> SEQ ID NO 3
<211> LENGTH: 20
<212> TYPE: DNA
<213> ORGANISM: artificial
<220> FEATURE:
<223> OTHER INFORMATION: PCR forward primer for porcine IL-8

<400> SEQUENCE: 3
tggcagtttt cctgctttct                20

<210> SEQ ID NO 4
<211> LENGTH: 20
<212> TYPE: DNA
<213> ORGANISM: artificial
<220> FEATURE:
<223> OTHER INFORMATION: PCR reverse primer porcine IL-8

<400> SEQUENCE: 4
cagtggggtc cactctcaat                20

<210> SEQ ID NO 5

```
<211> LENGTH: 20
<212> TYPE: DNA
<213> ORGANISM: artificial
<220> FEATURE:
<223> OTHER INFORMATION: PCR forward primer porcine IFN-gamma

<400> SEQUENCE: 5
ccattcaaag gagcatggat                                              20

<210> SEQ ID NO 6
<211> LENGTH: 20
<212> TYPE: DNA
<213> ORGANISM: artificial
<220> FEATURE:
<223> OTHER INFORMATION: PCR reverse primer porcine IFN-gamma

<400> SEQUENCE: 6
gagttcactg atggctttgc                                              20

<210> SEQ ID NO 7
<211> LENGTH: 20
<212> TYPE: DNA
<213> ORGANISM: artificial
<220> FEATURE:
<223> OTHER INFORMATION: PCR forward primer porcine IL-1Beta

<400> SEQUENCE: 7
caaaggccgc caagatataa                                              20

<210> SEQ ID NO 8
<211> LENGTH: 19
<212> TYPE: DNA
<213> ORGANISM: artificial
<220> FEATURE:
<223> OTHER INFORMATION: PCR reverse primer porcine IL-1Beta

<400> SEQUENCE: 8
gaaattcagg cagcaacat                                               19

<210> SEQ ID NO 9
<211> LENGTH: 20
<212> TYPE: DNA
<213> ORGANISM: artificial
<220> FEATURE:
<223> OTHER INFORMATION: PCR forward primer porcine IL-17

<400> SEQUENCE: 9
tcatgatccc acaaagtcca                                              20

<210> SEQ ID NO 10
<211> LENGTH: 20
<212> TYPE: DNA
<213> ORGANISM: artificial
<220> FEATURE:
<223> OTHER INFORMATION: PCR reverse primer porcine IL-17

<400> SEQUENCE: 10
agtccatggt gaggtgaagc                                              20

<210> SEQ ID NO 11
<211> LENGTH: 20
<212> TYPE: DNA
<213> ORGANISM: artificial
<220> FEATURE:
<223> OTHER INFORMATION: PCR forward primer porcine IL-10

<400> SEQUENCE: 11
```
tgatggggag gatatcaagg                                              20

<210> SEQ ID NO 12
<211> LENGTH: 20
<212> TYPE: DNA
<213> ORGANISM: artificial
<220> FEATURE:
<223> OTHER INFORMATION: PCR reverse primer porcine IL-10

<400> SEQUENCE: 12
tggagcttgc taaaggcact                                              20

<210> SEQ ID NO 13
<211> LENGTH: 20
<212> TYPE: DNA
<213> ORGANISM: artificial
<220> FEATURE:
<223> OTHER INFORMATION: PCR forward primer porcine TGF-Beta

<400> SEQUENCE: 13
cgagccctgg ataccaacta                                              20

<210> SEQ ID NO 14
<211> LENGTH: 20
<212> TYPE: DNA
<213> ORGANISM: artificial
<220> FEATURE:
<223> OTHER INFORMATION: PCR reverse primer porcine TGF-Beta

<400> SEQUENCE: 14
aggctccaga tgtagggaca                                              20

<210> SEQ ID NO 15
<211> LENGTH: 20
<212> TYPE: DNA
<213> ORGANISM: artificial
<220> FEATURE:
<223> OTHER INFORMATION: PCR forward primer porcine IL-12p

<400> SEQUENCE: 15
tttcagaccc gacgaactct                                              20

<210> SEQ ID NO 16
<211> LENGTH: 20
<212> TYPE: DNA
<213> ORGANISM: artificial
<220> FEATURE:
<223> OTHER INFORMATION: PCR reverse primer porcine IL-12p

<400> SEQUENCE: 16
cattggggta ccagtccaac                                              20

<210> SEQ ID NO 17
<211> LENGTH: 20
<212> TYPE: DNA
<213> ORGANISM: artificial
<220> FEATURE:
<223> OTHER INFORMATION: PCR forward primer porcine Foxp3

<400> SEQUENCE: 17
ctgacaaggg ttcctgctgt                                              20

<210> SEQ ID NO 18
<211> LENGTH: 20
<212> TYPE: DNA

-continued

```
<213> ORGANISM: artificial
<220> FEATURE:
<223> OTHER INFORMATION: PCR reverse primer porcine Foxp3

<400> SEQUENCE: 18
gaaatctggg aacgtgctgt                                                20

<210> SEQ ID NO 19
<211> LENGTH: 20
<212> TYPE: DNA
<213> ORGANISM: artificial
<220> FEATURE:
<223> OTHER INFORMATION: PCR forward primer porcine MUC1

<400> SEQUENCE: 19
accaagtccc ctaacccatc                                                20

<210> SEQ ID NO 20
<211> LENGTH: 20
<212> TYPE: DNA
<213> ORGANISM: artificial
<220> FEATURE:
<223> OTHER INFORMATION: PCR reverse primer porcine MUC1

<400> SEQUENCE: 20
ttggaatttt ccaggcagtc                                                20

<210> SEQ ID NO 21
<211> LENGTH: 20
<212> TYPE: DNA
<213> ORGANISM: artificial
<220> FEATURE:
<223> OTHER INFORMATION: PCR forward primer porcine MUC1

<400> SEQUENCE: 21
acccgcacta tgtcaccttc                                                20

<210> SEQ ID NO 22
<211> LENGTH: 20
<212> TYPE: DNA
<213> ORGANISM: artificial
<220> FEATURE:
<223> OTHER INFORMATION: PCR reverse primer porcine MUC2

<400> SEQUENCE: 22
gggatcgcag tggtagttgt                                                20
```